(12) United States Patent
Ahner et al.

(10) Patent No.: US 10,388,320 B2
(45) Date of Patent: Aug. 20, 2019

(54) APPARATUS AND METHODS USING INTERFERENCE IN LIGHT REFLECTED FROM ARTICLES

(71) Applicant: Seagate Technology LLC, Cupertino, CA (US)

(72) Inventors: Joachim Ahner, Livermore, CA (US); David Tung, Livermore, CA (US)

(73) Assignee: Seagate Technology LLC, Cupertino, CA (US)

( * ) Notice: Subject to any disclaimer, the term of this patent is extended or adjusted under 35 U.S.C. 154(b) by 105 days.

(21) Appl. No.: 15/301,294

(22) PCT Filed: Apr. 6, 2015

(86) PCT No.: PCT/US2015/024580
§ 371 (c)(1),
(2) Date: Sep. 30, 2016

(87) PCT Pub. No.: WO2015/157197
PCT Pub. Date: Oct. 15, 2015

(65) Prior Publication Data
US 2017/0025149 A1    Jan. 26, 2017

Related U.S. Application Data

(60) Provisional application No. 61/976,496, filed on Apr. 7, 2014.

(51) Int. Cl.
*G01B 9/02*    (2006.01)
*G11B 20/18*   (2006.01)
(Continued)

(52) U.S. Cl.
CPC ......... *G11B 20/1816* (2013.01); *G01N 21/21* (2013.01); *G01N 21/55* (2013.01);
(Continued)

(58) Field of Classification Search
CPC .... G11B 20/1816; G01N 21/21; G01N 21/55; G01N 21/88; G01N 21/8806;
(Continued)

(56) References Cited

U.S. PATENT DOCUMENTS 6,124,930 A * 9/2000 Fercher .............. G01N 21/4795
356/497
6,169,631 B1   1/2001 Xuan et al.
(Continued)

OTHER PUBLICATIONS

PCT/US2015/024580—PCT International Search Report, dated Jun. 18, 2015, ISA/KR, Authorized Officer Sung Cheal Byun.
(Continued)

*Primary Examiner* — Kara E. Geisel
*Assistant Examiner* — Jonathon Cook

(57) ABSTRACT

Provided herein are apparatus and methods for inspecting articles for features using interference in light reflected from the articles. The interference may be used to detect, distinguish, and/or map features of articles, which features may include, but are not limited to, surface defects. In at least one embodiment, an apparatus and method includes conveying parallel light along a primary axis through a telecentric lens and a light-splitting device, respectively; illuminating a majority of a surface of an article with the parallel light; conveying reflected light from the surface of the article along the primary axis back through the light-splitting device and the telecentric lens, respectively; and recording interference resulting from a combination of light comprising at least the reflected light from the surface of the article.

20 Claims, 13 Drawing Sheets

Figure 1:
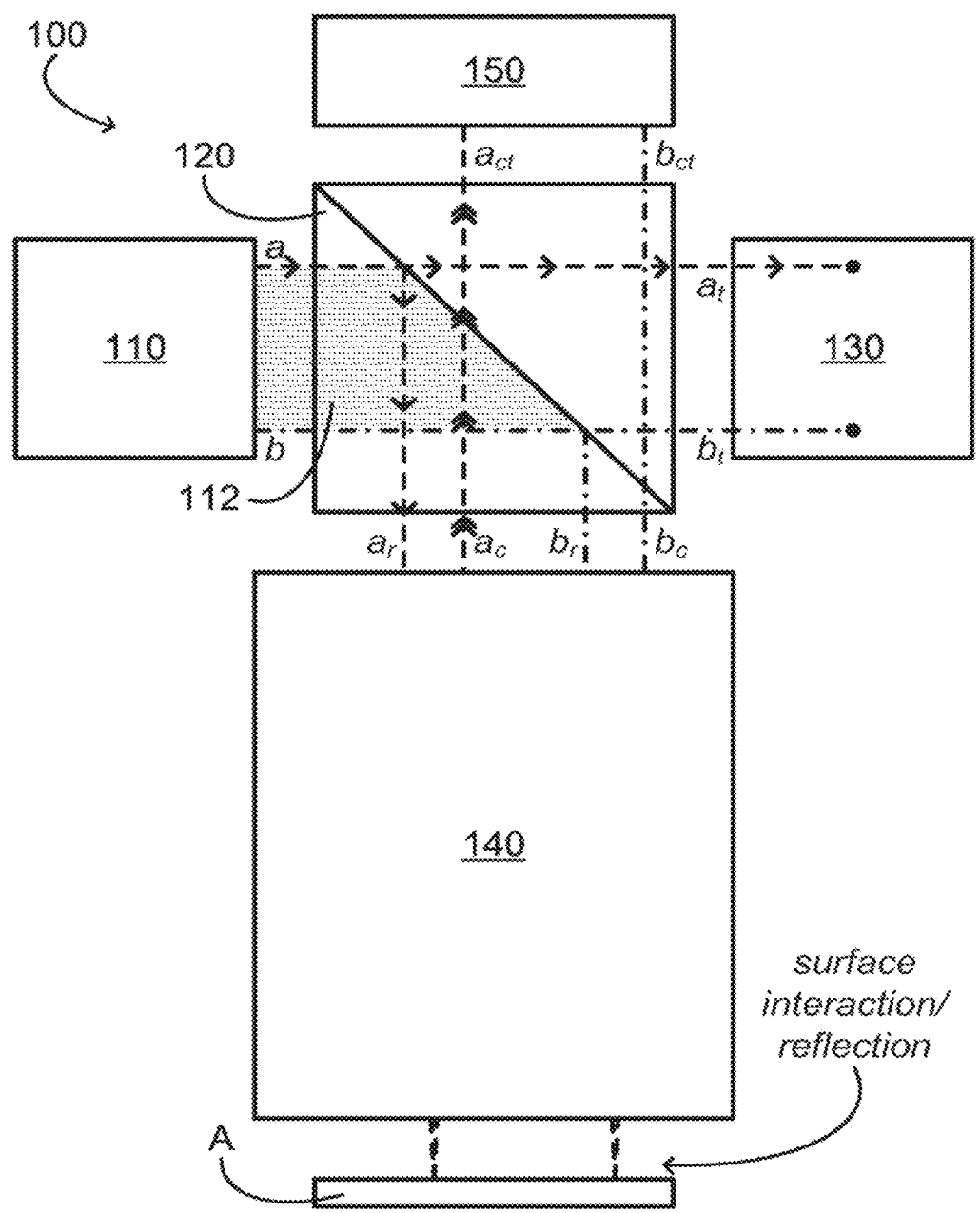

(51) Int. Cl.
    *G01N 21/88*   (2006.01)
    *G01N 21/21*   (2006.01)
    *G01N 21/55*   (2014.01)
    *G01N 21/95*   (2006.01)
(52) U.S. Cl.
    CPC ......... *G01N 21/8806* (2013.01); *G01N 21/95* (2013.01); *G01B 9/02* (2013.01); *G01B 2290/70* (2013.01); *G01N 21/9501* (2013.01); *G01N 21/9506* (2013.01); *G01N 2021/8848* (2013.01); *G01N 2201/06113* (2013.01)
(58) Field of Classification Search
    CPC ............... G01N 21/95; G01N 21/9501; G01N 21/9506; G01N 2021/8848; G01N 2201/06113; G01B 9/02; G01B 2290/70; G01B 11/2441; G03F 7/7065; G02B 13/22
    USPC .................................................. 356/491, 496
    See application file for complete search history.

(56) References Cited

U.S. PATENT DOCUMENTS

| | | | | |
|---|---|---|---|---|
| 6,392,752 | B1* | 5/2002 | Johnson | B82Y 10/00 356/511 |
| 6,419,360 | B1* | 7/2002 | Hauger | G01B 11/00 351/206 |
| 6,937,345 | B2* | 8/2005 | Kuramoto | G01M 11/0242 356/515 |
| 6,970,253 | B2* | 11/2005 | Lindner | G02B 13/06 356/241.1 |
| 7,041,998 | B2 | 5/2006 | Weiss et al. | |
| 7,061,625 | B1* | 6/2006 | Hwang | G01B 11/2441 356/497 |
| 2003/0016901 | A1* | 1/2003 | Cormack | G01J 3/0218 385/15 |
| 2004/0012791 | A1* | 1/2004 | Lega | G01B 9/0209 356/497 |
| 2006/0007448 | A1* | 1/2006 | Hwang | G01N 21/47 356/512 |
| 2007/0091317 | A1* | 4/2007 | Freischlad | G01B 11/0675 356/511 |
| 2007/0263226 | A1* | 11/2007 | Kurtz | A61B 5/0059 356/492 |
| 2008/0304071 | A1* | 12/2008 | Kallmann | G01N 21/45 356/450 |
| 2009/0086216 | A1* | 4/2009 | Marks | G01N 21/4795 356/511 |
| 2011/0032504 | A1* | 2/2011 | Sasaki | G01B 11/2441 355/72 |
| 2011/0075151 | A1 | 3/2011 | Jeong | |
| 2012/0206703 | A1 | 8/2012 | Bhattacharyya et al. | |
| 2012/0224183 | A1 | 9/2012 | Fay et al. | |

OTHER PUBLICATIONS

PCT International Preliminary Report on Patentability (Chapter I) dated Oct. 20, 2016 in International Application No. PCT/US2015/024580. 8 pages.

* cited by examiner

US 10,388,320 B2

APPARATUS AND METHODS USING INTERFERENCE IN LIGHT REFLECTED FROM ARTICLES

CROSS REFERENCE

This application claims the benefit of U.S. Provisional Patent Application No. 61/976,496, filed Apr. 7, 2014.

BACKGROUND

An article may be inspected for defects that might degrade the performance of the article or a system including the article. For example, a hard disk for a hard disk drive may be fabricated and inspected for defects that might degrade the performance of the hard disk or the hard disk drive. Accordingly, apparatus and methods may be used to inspect articles for defects.

SUMMARY

Provided herein are apparatus and methods for inspecting articles for features using interference in light reflected from the articles. The interference may be used to detect, distinguish, and/or map features of articles, which features may include, but are not limited to, surface defects.

In at least one embodiment, an apparatus and method includes conveying parallel light along a primary axis through a telecentric lens and a light-splitting device, respectively; illuminating a majority of a surface of an article with the parallel light; conveying reflected light from the surface of the article along the primary axis back through the light-splitting device and the telecentric lens, respectively; and recording interference resulting from a combination of light comprising at least the reflected light from the surface of the article.

These and various other features will be apparent from a reading of the following description.

DRAWINGS

FIG. 1 provides a schematic illustrating an apparatus for inspecting articles for features according to one or more embodiments.

Figure 2:
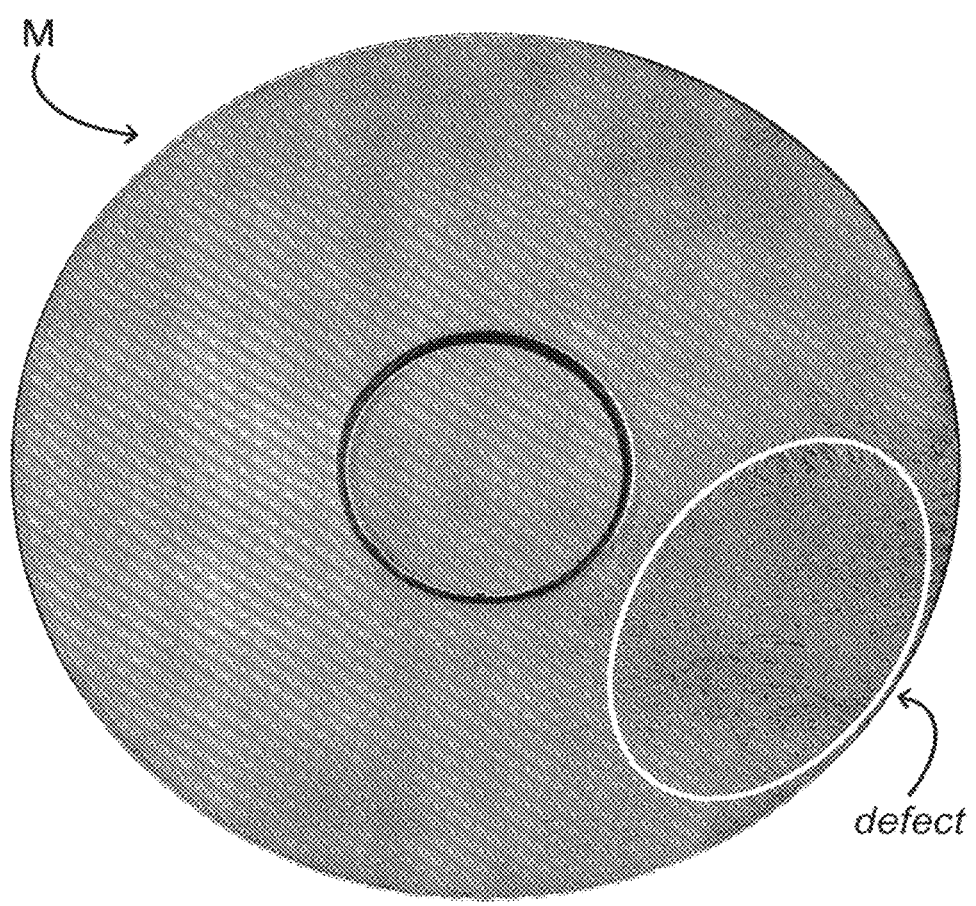

FIG. 2 provides a features map for a surface of an article according to one or more embodiments.

Figure 3A:
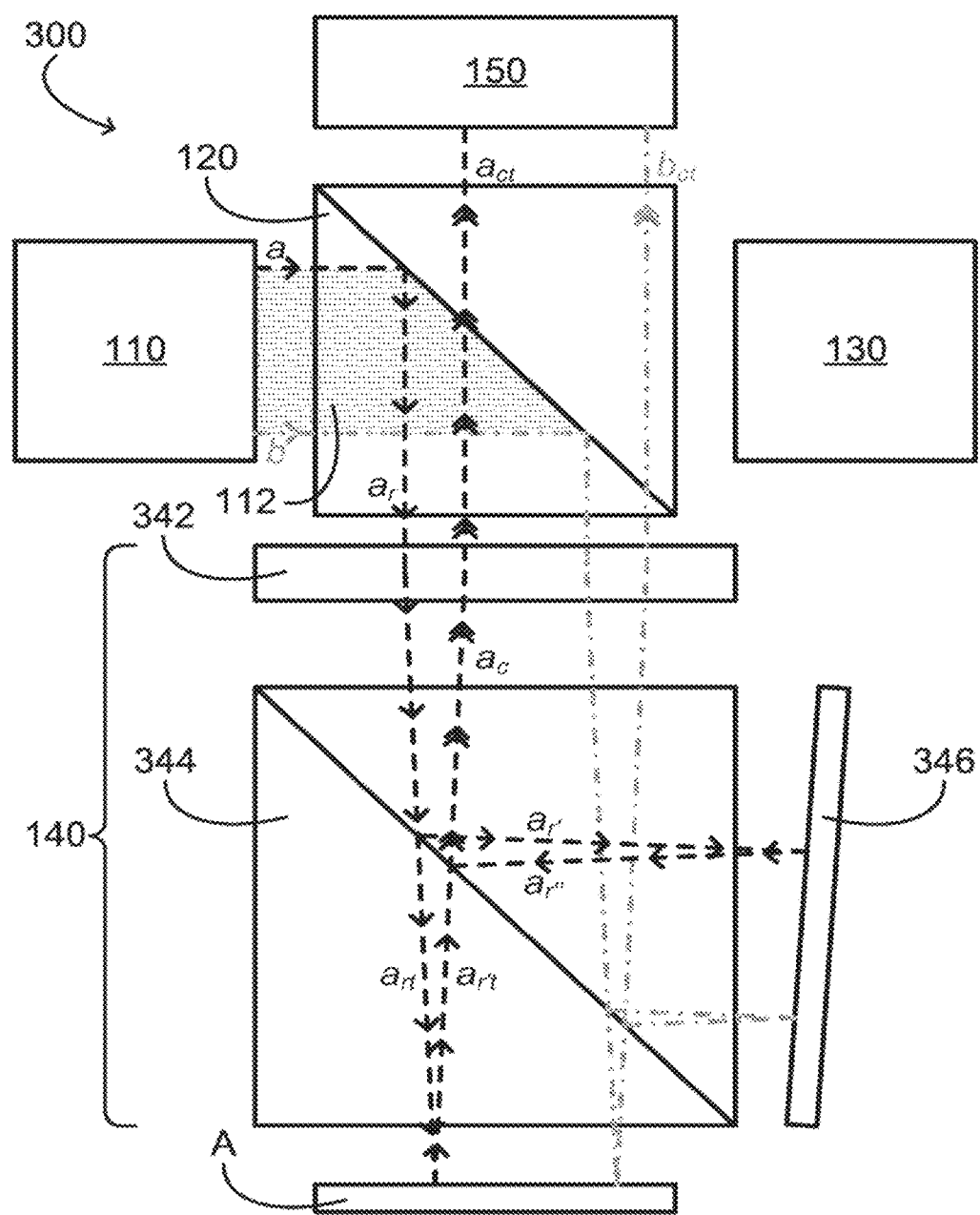

FIG. 3A provides a schematic illustrating an apparatus for inspecting articles for features according to one or more embodiments.

Figure 3B:
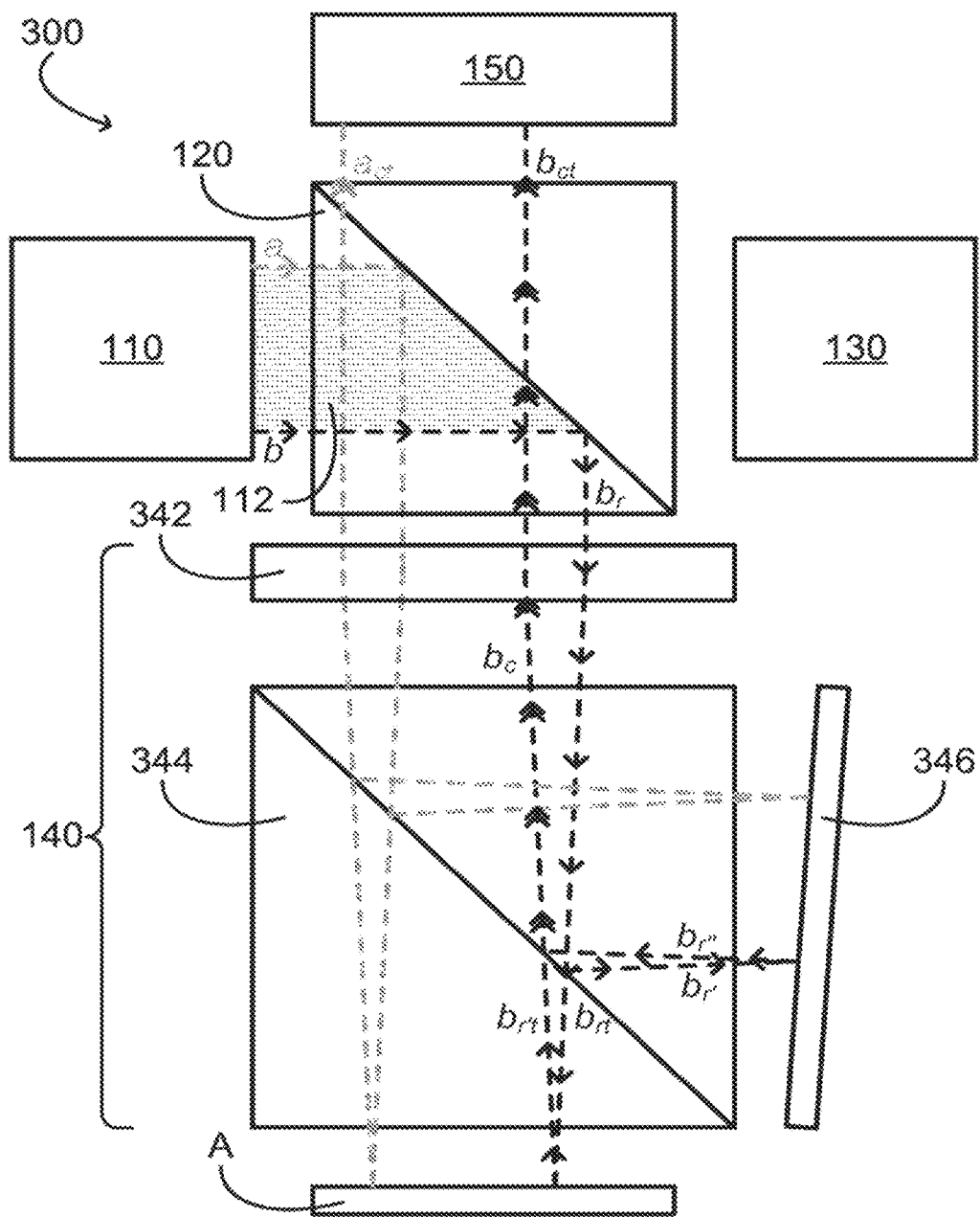

FIG. 3B provides a schematic illustrating an apparatus for inspecting articles for features according to one or more embodiments.

Figure 4:
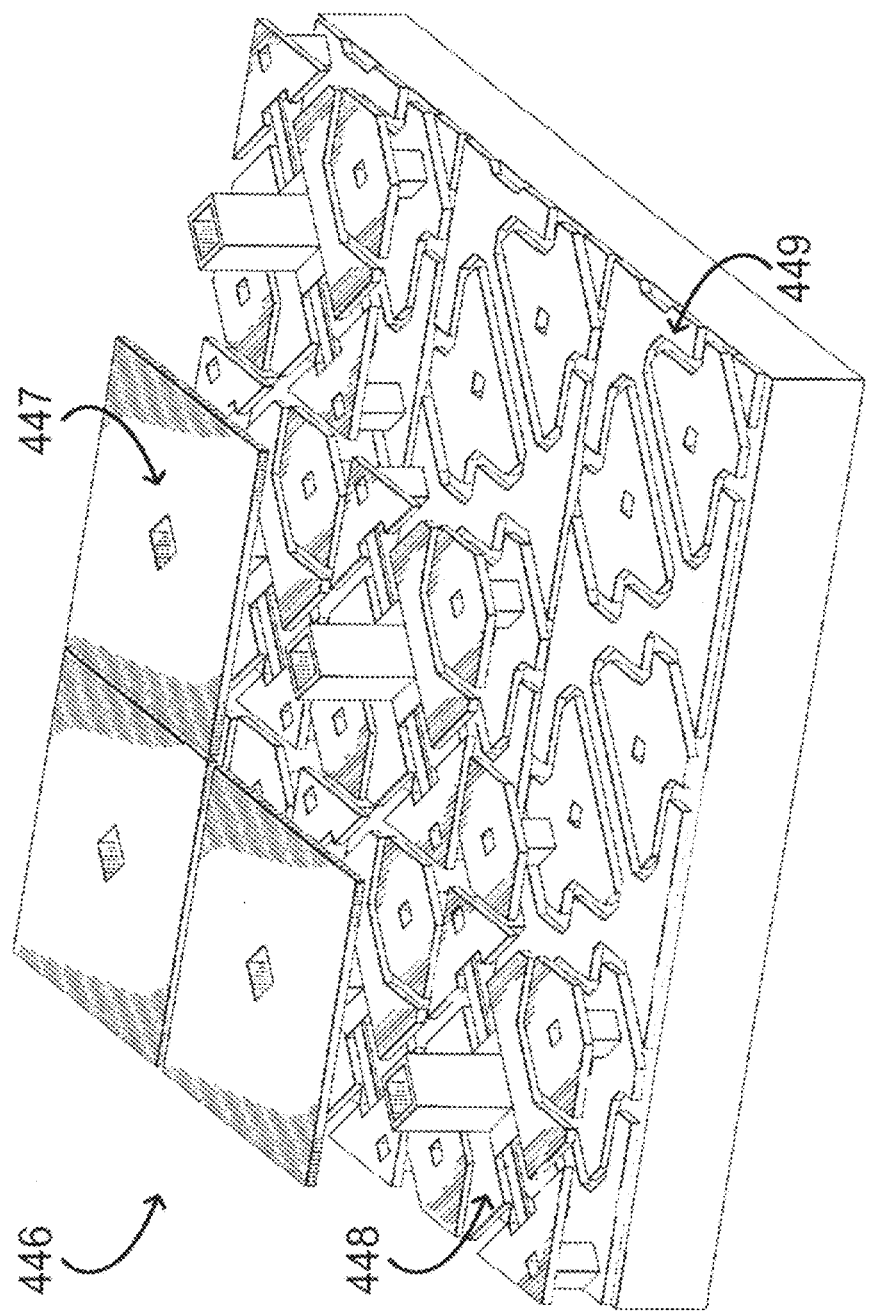

FIG. 4 provides a digital micromirror device for an apparatus for inspecting articles for features according to one or more embodiments.

Figure 5:
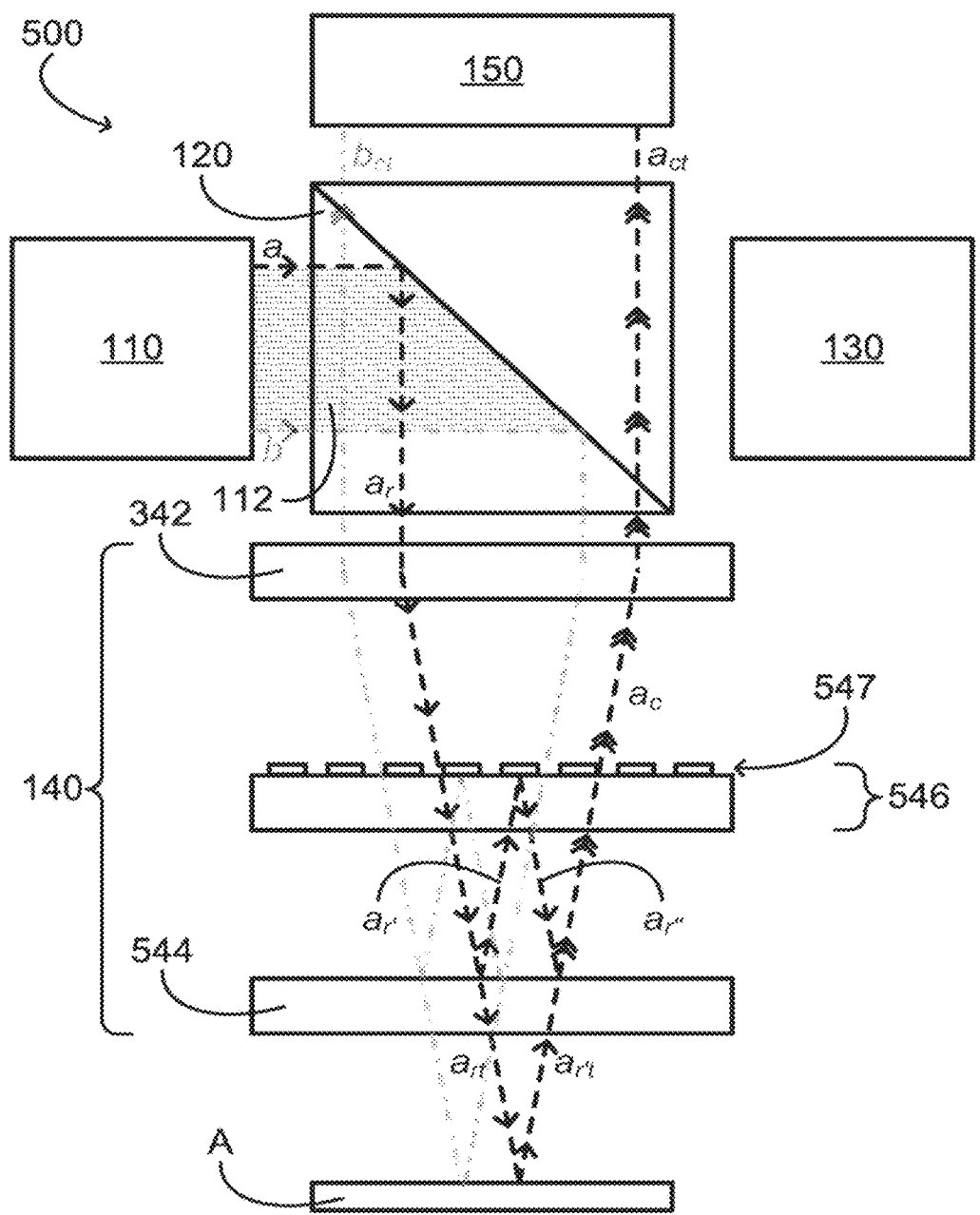

FIG. 5 provides a schematic illustrating an apparatus for inspecting articles for features according to one or more embodiments.

Figure 6A:
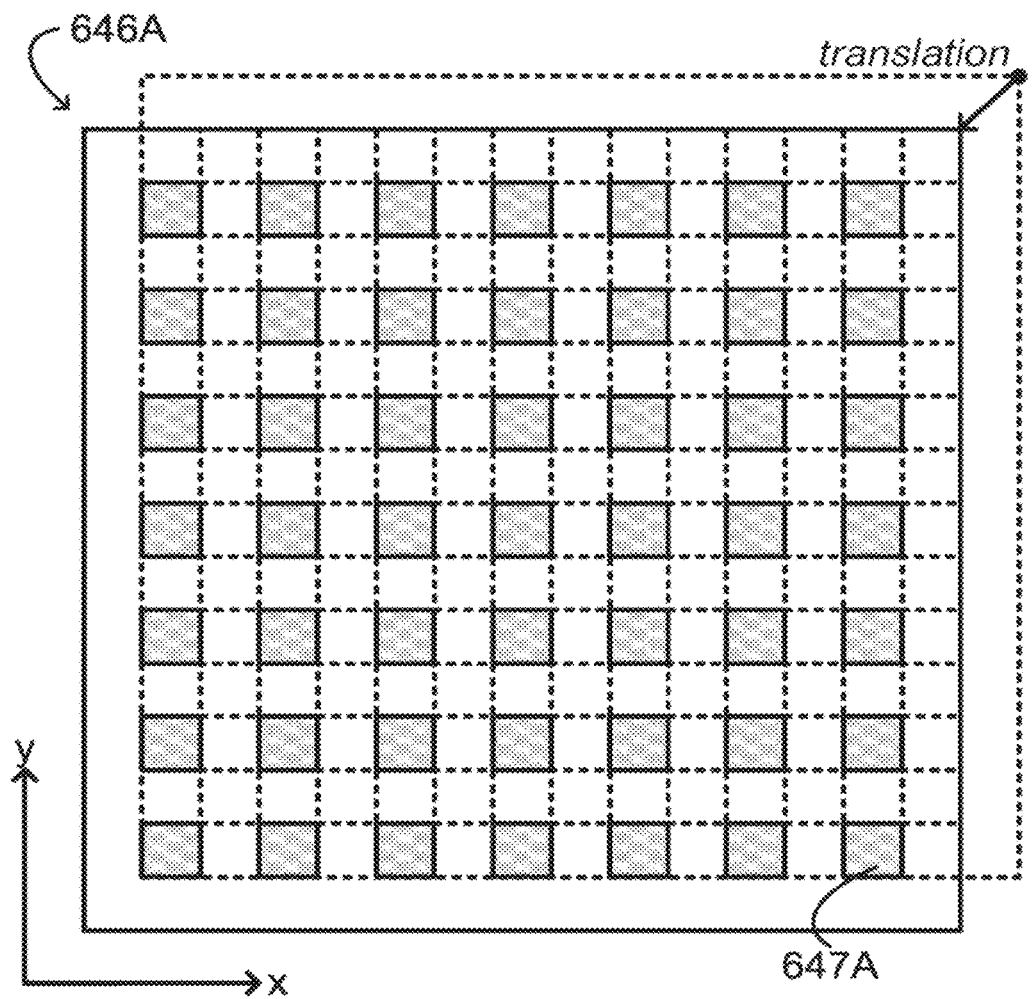

FIG. 6A provides a mirror array on an XY-positioning stage for an apparatus for inspecting articles for features according to one or more embodiments.

Figure 6B:
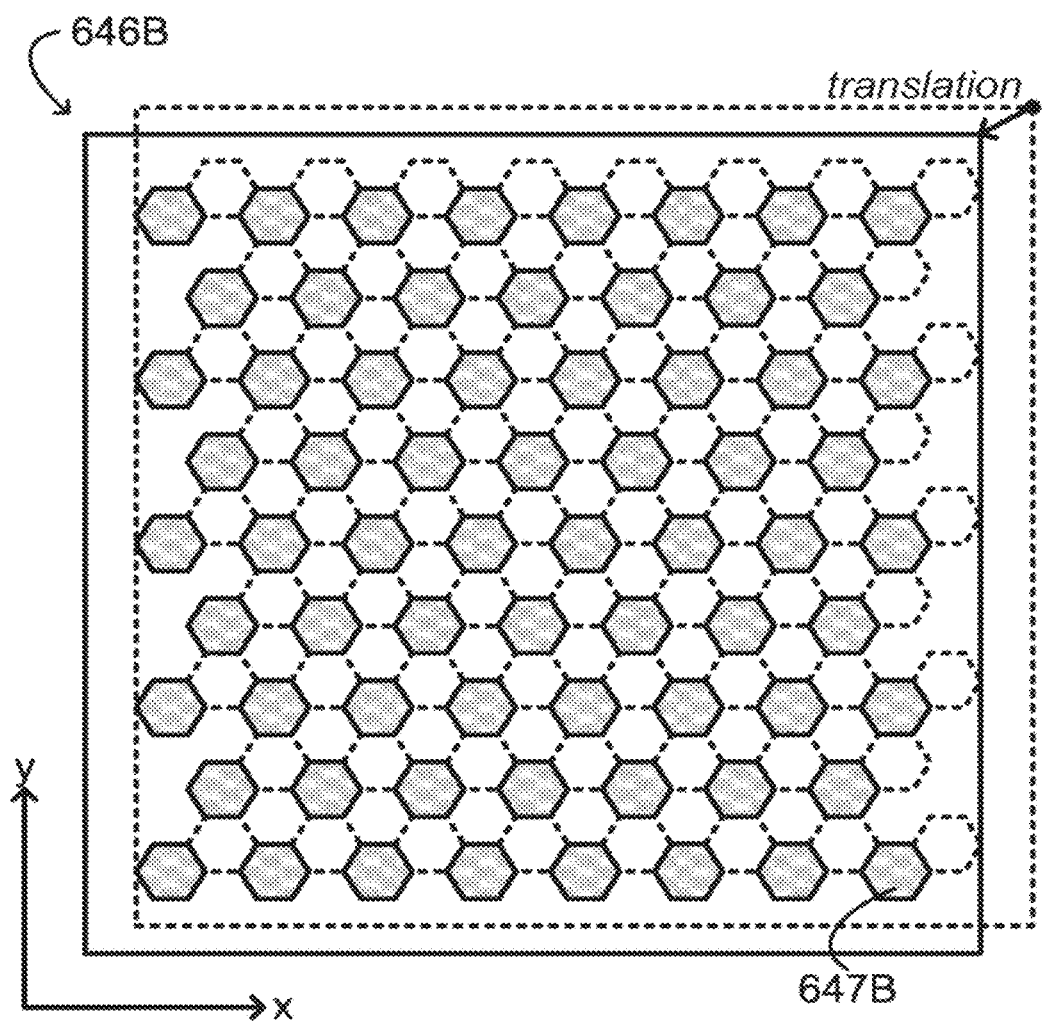

FIG. 6B provides a mirror array on an XY-positioning stage for an apparatus for inspecting articles for features according to one or more embodiments.

Figure 7A:
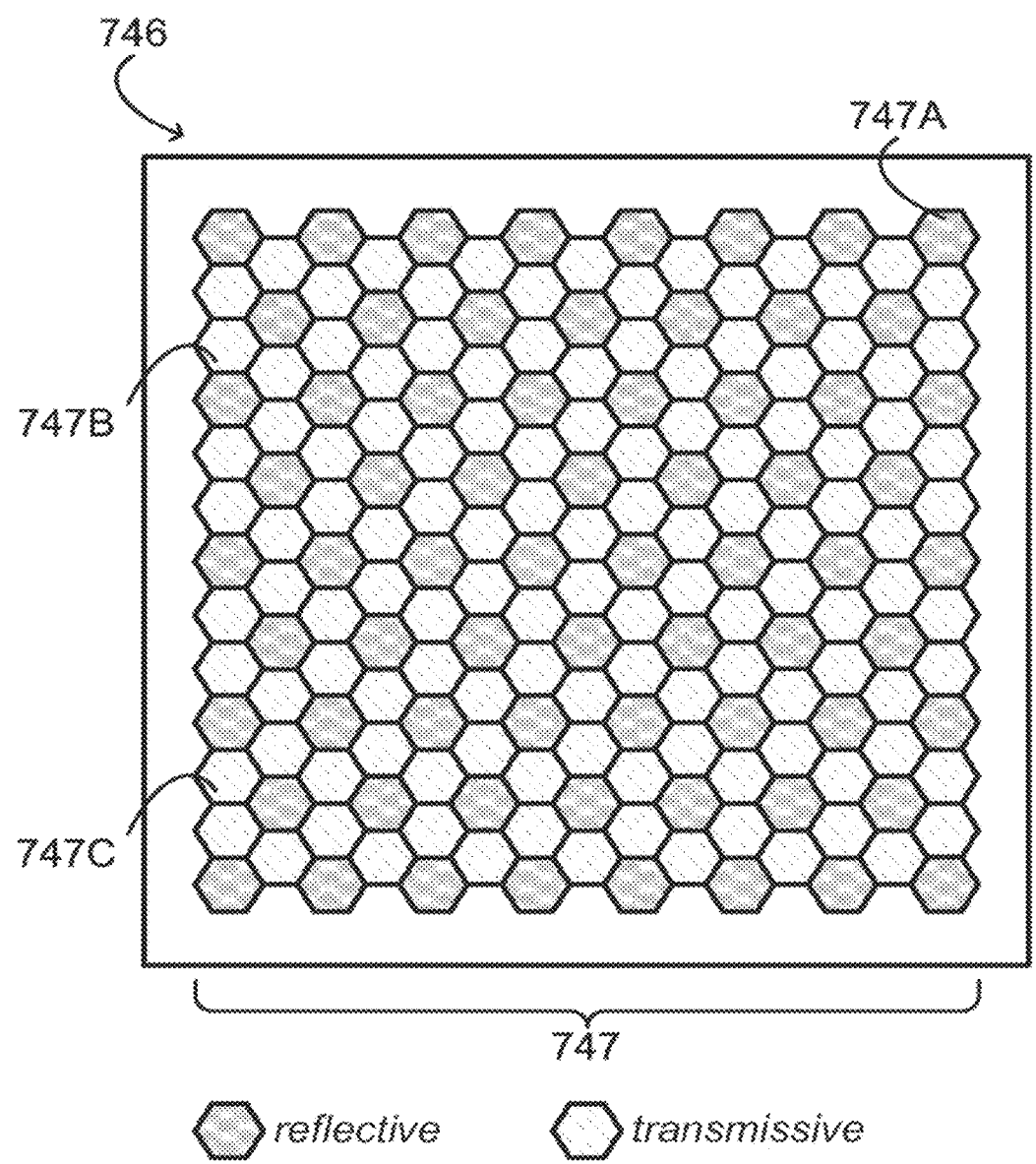

FIG. 7A provides a liquid crystal-based mirror array for an apparatus for inspecting articles for features according to one or more embodiments.

Figure 7B:
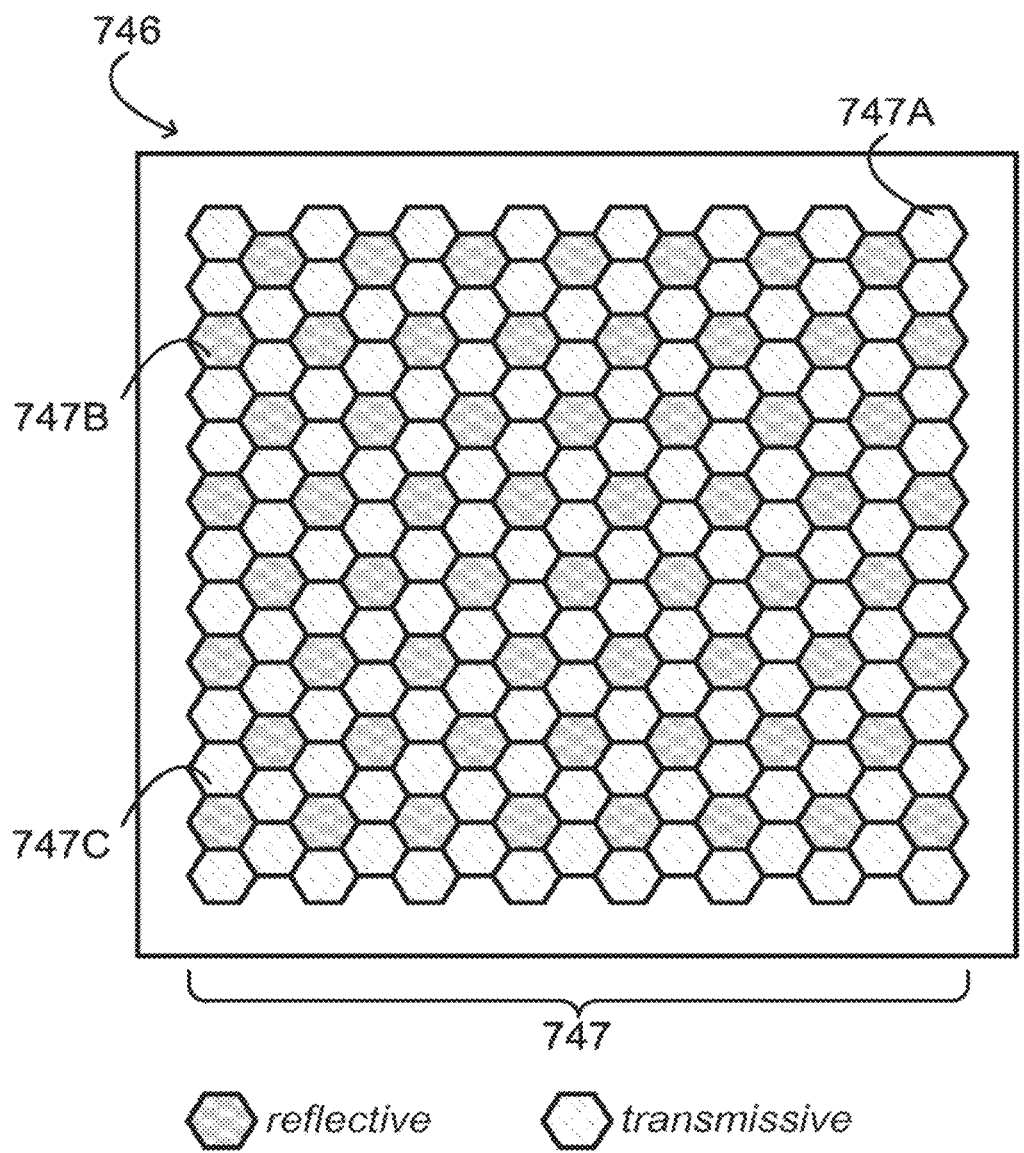

FIG. 7B provides a liquid crystal-based mirror array for an apparatus for inspecting articles for features according to one or more embodiments.

Figure 8:
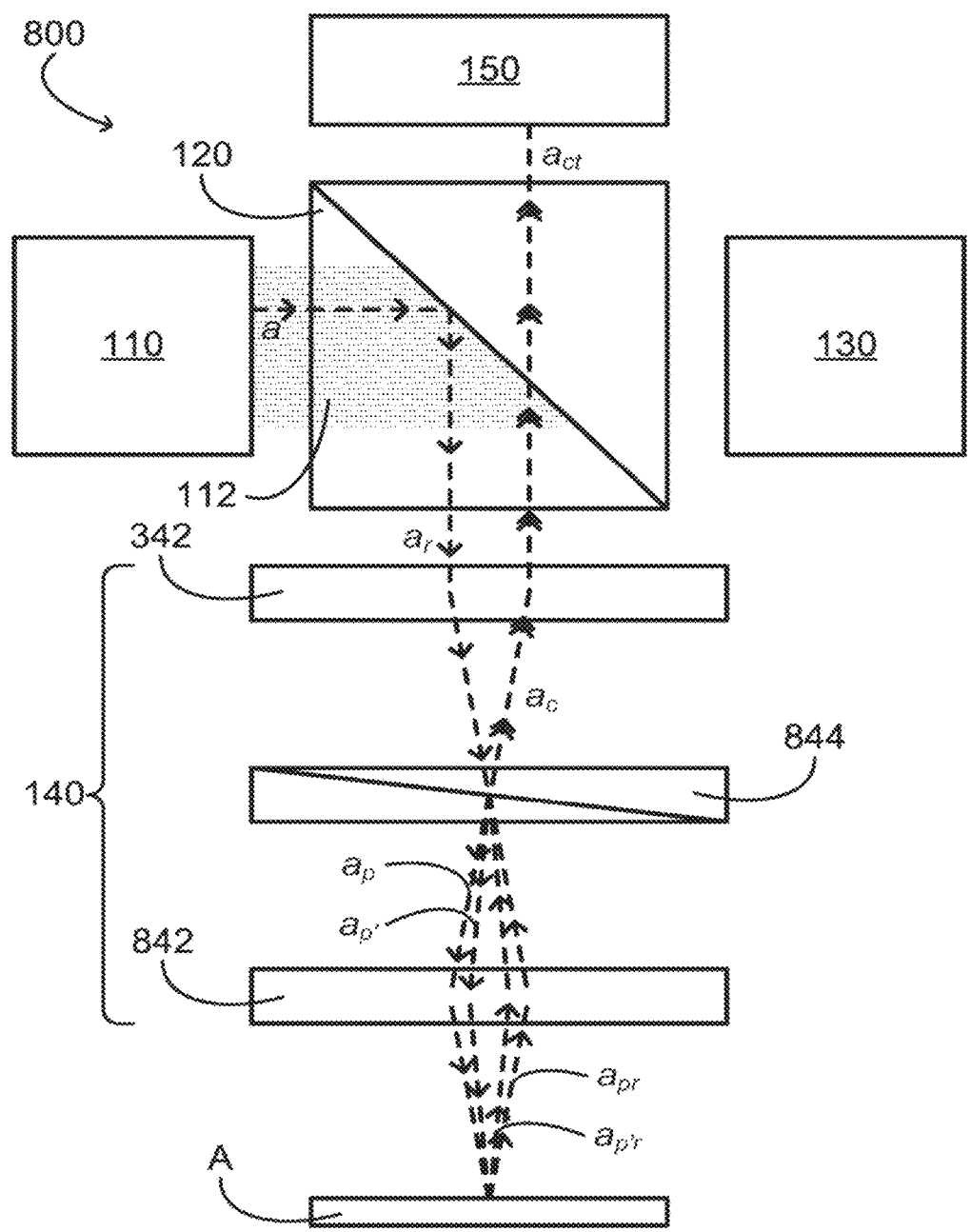

FIG. 8 provides a schematic illustrating an apparatus for inspecting articles for features according to one or more embodiments.

Figure 9A:
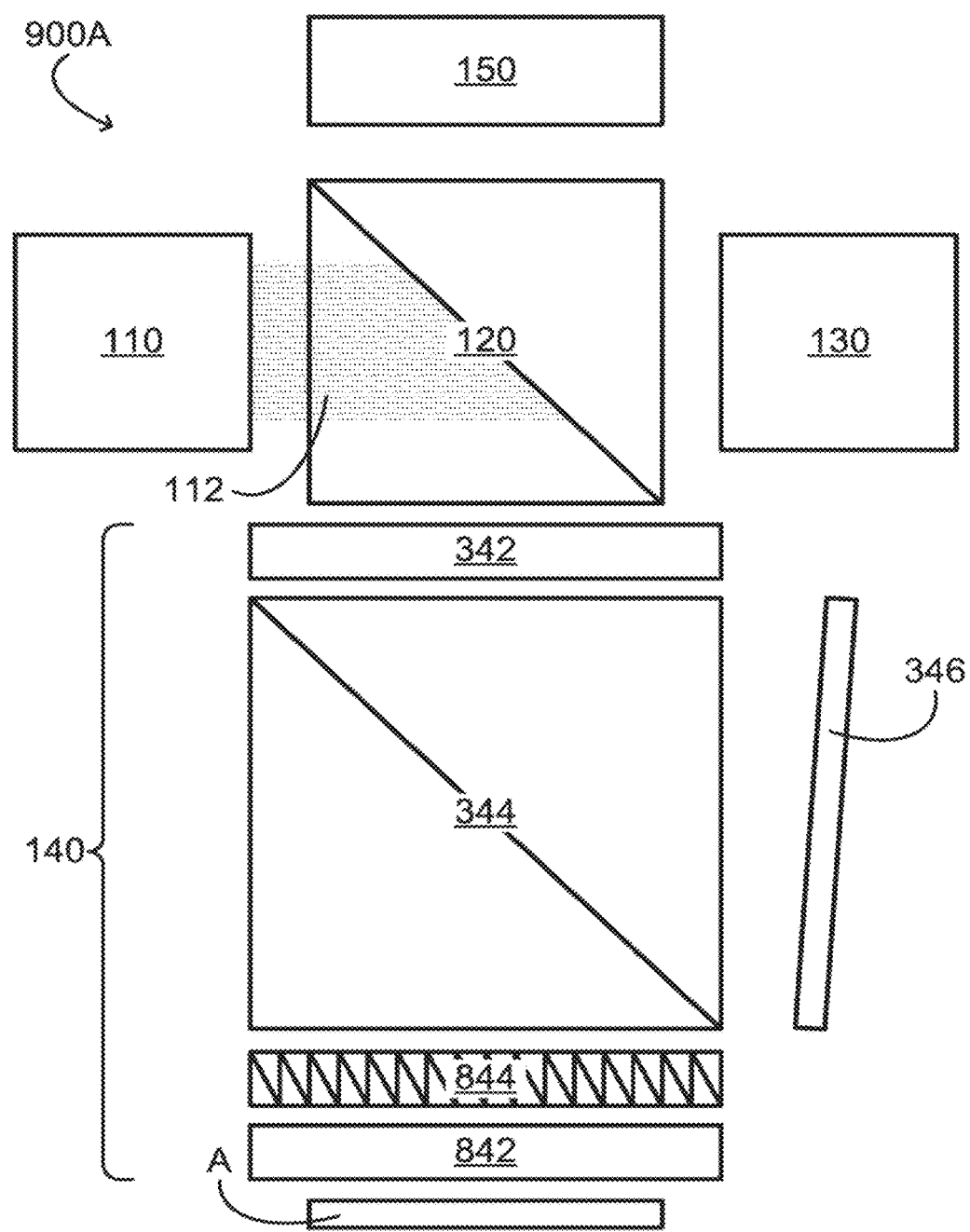

FIG. 9A provides a schematic illustrating an apparatus for inspecting articles for features according to one or more embodiments.

Figure 9B:
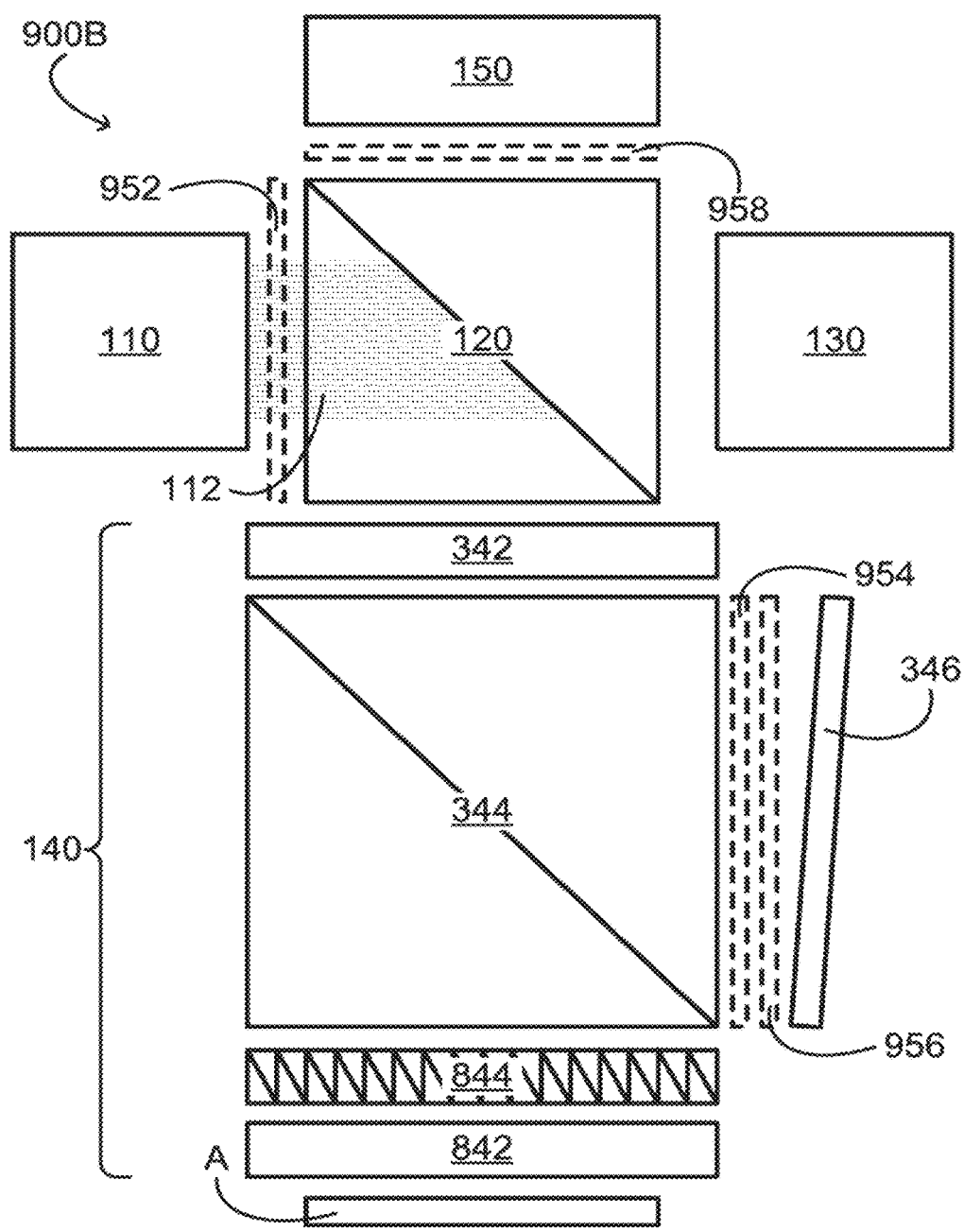

FIG. 9B provides a schematic illustrating an apparatus for inspecting articles for features according to one or more embodiments.

DESCRIPTION

Before some particular embodiments are provided in greater detail, it should be understood by persons having ordinary skill in the art that the particular embodiments provided herein do not limit the concepts provided herein, as features in such particular embodiments may vary. It should likewise be understood that a particular embodiment provided herein has features that may be readily separated from the particular embodiment and optionally combined with or substituted for features in any of several other embodiments provided herein.

It should also be understood by persons having ordinary skill in the art that the terminology used herein is for the purpose of describing some particular embodiments, and the terminology does not limit the concepts provided herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps need not necessarily appear in that order, and embodiments need not be necessarily limited to the three elements or steps. It should also be understood that, unless indicated otherwise, any labels such as "left," "right," "front." "back," "top," "bottom," "forward," "reverse," "clockwise," "counter-clockwise," "up," and "down," or other similar terms such as "upper," "lower," "aft," "fore," "vertical," "horizontal," "proximal," and "distal," or the like, are used for convenience and are not intended to imply, for example, any particular fixed location, orientation, or direction. Instead, such labels are used to reflect, for example, relative location, orientation, or direction. It should also be understood that the singular forms of "a," "an," and "the" include plural references unless the context clearly dictates otherwise.

Unless defined otherwise, all technical and scientific terms used herein have the same meaning as commonly understood by persons having ordinary skill in the art.

An article may be inspected for features including defects (e.g., surface and/or subsurface defects) that might degrade the performance of the article or a system including the article. The article may include any article of manufacture or a workpiece thereof in any stage of manufacture having one or more surfaces or subsurfaces operable to reflect light. For example, the article may include, but is not limited to, a semiconductor wafer, a magnetic recording medium (e.g., a hard disk for a hard disk drive), a magnetic recording read-write head or slider therefor, or a workpiece thereof in any stage of manufacture.

A hard disk or a workpiece thereof may be inspected for features including defects (e.g., surface and/or subsurface defects including magnetic defects) that might degrade the performance of the hard disk or the hard disk drive. For example, a hard disk or a workpiece thereof may be inspected for thermal asperities, pits, shallow surface defects, waviness, and/or the like. For example, a hard disk or a workpiece thereof having a lubricant layer may be inspected for lubricant layer inhomogeneity including lubricant layer smears, ripples, bumps, and/or depletion. For example, a hard disk or a workpiece thereof having a carbon overcoat layer may be inspected for carbon overcoat inhomogeneity including carbon overcoat layer voids and/or shadows (e.g., shadows from sputtering clamps).

It is important to inspect articles for features including performance-degrading defects in order to correct manufacturing trends and to increase product quality.

Provided herein are apparatus and methods for inspecting articles for features using interference in light reflected from the articles. The interference may be used to detect, distinguish, and/or map features of articles, which features may include, but are not limited to, surface defects. Apparatus and methods for inspecting articles for features using interference in light reflected from the articles will now be provided in some particular, non-limiting embodiments.

FIG. 1 provides a schematic illustrating an apparatus 100 including a number of components for inspecting articles for features using interference in light reflected from the articles. As shown in FIG. 1, the apparatus 100 may include, but is not limited to, a light source 110, a light-splitting device 120, a light trap 130, an interferometric optical assembly 140, and a recording device 150. As further shown in FIG. 1, an article A may be positioned under the apparatus 100 where light from the apparatus 100 may illuminate, interact with, and be reflected by a surface of the article A.

While not shown in FIG. 1, the apparatus 100 may further include a stage configured to support the article A and hold the article A stationary during inspection without, for example, translation or rotation. However, the stage may be optionally further configured to translate and/or rotate the article A during inspection. With respect to translation, the stage may be optionally further configured as a piezoelectric, XY-positioning stage such that article A may be translated in any XY-related direction over a distance corresponding to a sub-pixel-sized distance, a pixel-sized distance, or a multiple pixel-sized distance, wherein a pixel-sized distance corresponds to pixel size or pixel pitch in an image sensor of an imaging device. A piezoelectric, XY-positioning stage may be used in combination with any of various embodiments of the mirror array 546 provided herein, for example, to translate the article A with respect to the mirror array 546. With respect to rotation, the stage may be optionally further configured to rotate the article A for piecewise inspection of the article A; however, it should be understood that piecewise inspection may affect throughput.

With respect to the light source 110, the light source 110 may be used alone or in combination with one or more additional optical components provided herein in a light source assembly. As such, it should be understood that any reference to the light source 110 used herein may include the light source 110 alone or the light source 110 in combination with one or more additional optical components provided herein in a light source assembly.

The light source 110 may be configured to provide parallel light 112, wherein light rays of the parallel light minimally diverge as the light propagates through the apparatus 100. The light source 110 may be further configured to provide substantially homogeneous light, wherein the same or about the same radiant energy (e.g., radiant energy as measured in joules or J) is provided to each illuminated surface location at a specific time or over a specific time interval, wherein the same or about the same radiant energy per unit time (e.g., radiant power as measured in watts or W or J/s) is provided to each illuminated surface location, and/or wherein the same or about the same radiant power per unit area (e.g., irradiance as measured in $W/m^2$) is provided to each illuminated surface location.

The light source 110 may be configured to provide light including, but not limited to, one or more qualities of light selected from the following: a relatively wide range of wavelengths (e.g., whole spectrum, broad spectrum, ultraviolet-visible, visible, infrared, etc.) of light, a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.) of light, or a particular wavelength (e.g., monochromatic) of light; a relatively wide range of frequencies (e.g., whole spectrum, broad spectrum, ultraviolet-visible, visible, infrared, etc.) of light, a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.) of light, or a particular frequency (e.g., monochromatic) of light; unpolarized light or polarized light, wherein the polarized light includes linearly polarized light (e.g., p-polarized light, s-polarized light, q-polarized light, etc.), circularly polarized light, or elliptically polarized light; certain degrees of spatially and/or temporally coherent light ranging from noncoherent light to coherent light (e.g., laser); and collimated or telecentric light.

The light source 110 may be configured to provide light to illuminate a portion of the surface of the article A up to and including an entire surface of the article A. As such, the light source 110 may be configured to provide light to illuminate a substantial portion of the surface (e.g., ≥10% of the surface) of the article A, a major portion of the surface (e.g., >50% of the surface) of the article A, nearly the entire surface (e.g., ~100% of the surface) of the article A, or the entire surface (i.e., 100% of the surface) of the article A. It should be understood that any reference to the surface of the article A used herein may include the foregoing portion of the surface of the article A up to and including the entire surface of the article A, optionally including one or more subsurfaces.

With respect to the light-splitting device 120, the light-splitting device 120 may be used alone or in combination with one or more additional optical components provided herein in a light-splitting assembly. As such, it should be understood that any reference to the light-splitting device 120 used herein may include the light-splitting device 120 alone or the light-splitting device 120 in combination with one or more additional optical components provided herein in a light-splitting assembly.

The light-splitting device 120 may include, but is not limited to, any light-splitting block, plate, or pellicle operable to split incident light in accordance with at least FIG. 1. The light-splitting device 120 may reflect a first portion of the incident light and transmit a second portion of the incident light in accordance with composition, construction, or the composition and construction of the light-splitting device 120, wherein the composition includes substrate, bonding, and/or coating compositions of the light-splitting device 120, and wherein the construction includes the manner in which one or more of the foregoing is assembled into the light-splitting device 120. The composition and/or construction of the light-splitting device 120 may be such that the first and second portions of the incident light are respectively reflected and transmitted in a particular reflection/ transmission ("R/T") ratio (e.g., R/T of 10/90, 30/70, 50/50, 70/30, or 90/10). Additionally or alternatively, the composition and/or construction of the light-splitting device 120 may be such that the first and second portions of the incident light are respectively reflected and transmitted with different polarization states. For example, the light-splitting device 120 may reflect s-polarized light and transmit p-polarized light.

With respect to the light trap 130, the light trap 130 may be used alone or in combination with one or more additional optical components provided herein in a light-trapping assembly. As such, it should be understood that any reference to the light trap 130 used herein may include the light trap 130 alone or the light trap 130 in combination with one or more additional optical components provided herein in a light-trapping assembly.

The light trap 130 may include, but is not limited to, any light block or light trap with a sufficiently sized aperture operable to absorb incident light in accordance with at least FIG. 1. The light trap 130 may include, but is not limited to, one or more absorptive materials selected from absorptive neutral density glass; blackout fabric; black-flocked paper; black posterboard: black hardboard; light-absorbing foil including black aluminum foil, Metal Velvet™ from Acktar Ltd., Scatter Black™ from Acktar Ltd.; anodized aluminum; graphite; and Vantablack® from Surrey NanoSystems Ltd.

With respect to the interferometric optical assembly 140, the interferometric optical assembly 140 may include, but is not limited to, one or more optical components for interferometry selected from the optical components for interferometry provided in FIGS. 3A, 3B, 4, 5, 6A, 6B, 7A, 7B, 8, 9A, and 9B and the description therefor.

With respect to the recording device 150, the recording device 150 may be used alone or in combination with one or more additional optical components provided herein in a recording assembly. As such, it should be understood that any reference to the recording device 150 used herein may include the recording device 150 alone or the recording device 150 in combination with one or more additional optical components provided herein in a recording assembly.

The recording device 150 may include, but is not limited to, an imaging device including an image sensor operable to detect the light provided to and subsequently reflected from the surface of the article A. The image sensor may include a number of light sensor elements or pixels, each of which may include a photodetector and one or more readout devices (e.g., capacitors, transistors, etc.) operable to convert detected light into electronic signals for processing by a processing means.

The number of pixels in the image sensor may include, but is not limited to, an arrangement of n rows and m columns of pixels in a two-dimensional array, and the number of pixels may be expressed in a resolution n×m of millions of pixels or megapixels ("MP"). For example, the number of pixels may be in an arrangement of 2048 rows and 2048 columns in a two-dimensional array, and the number of pixels may be expressed in a resolution of 4.2 MP (i.e., 2048 pixels×2048 pixels=4.2×$10^6$ pixels or 4.2 MP). For example, the number of pixels may be in an arrangement of 2560 rows and 2160 columns in a two-dimensional array, and the number of pixels may be expressed in a resolution of 5.5 MP (i.e., 2560 pixels×2160 pixels=5.5×$10^6$ pixels or 5.5 MP). It should be understood that the image sensor is not limited to the foregoing numbers of pixels as the image sensor may include more or fewer pixels than either of the foregoing numbers of pixels.

Each pixel of the image sensor may be, but is not limited to, a rectangle or square in shape, and each pixel may be, but is not limited to, micrometer sized (i.e., admits of μm units as measured) in at least one of a length or a width. For example, each pixel may be a rectangle in shape, and each pixel may be about 6.5 μm in at least one of a length or a width. For example, each pixel may be a square in shape, and each pixel may be about 6.5 μm in length and width. It should be understood that the image sensor is not limited to pixels of the foregoing shapes as the image sensor may include pixels of any of a number of shapes different than the foregoing shapes. It should be understood that the image sensor is not limited to pixels of the foregoing size as the image sensor may include pixels of any of a number of sizes (e.g., from about 3 μm to about 15 μm) different than the foregoing size.

Each pixel of the image sensor may correspond to a particular, fixed area of the surface of the article A, and each pixel may respectively correspond to a particular, fixed area of a features map (e.g., features map M of FIG. 2) of the surface of the article A. As such, there may be a one-to-one-to-one correspondence among the particular, fixed area of the surface of the article A, the pixel of the image sensor, and the particular, fixed area of the features map of the surface of the article A. Such correspondence facilitates identification of a particular feature's coordinates about the surface of the article A, optionally for further analysis.

The image sensor may include, but is not limited to, a charge-coupled device ("CCD"), an intensified charge-coupled device ("ICCD"), an electron-multiplying charge-coupled device ("EMCCD"), a complementary metal-oxide semiconductor ("CMOS"), or a scientific complementary metal-oxide semiconductor ("sCMOS"). And the imaging device may include, but is not limited to, a CCD camera, an ICCD camera, an EMCCD camera, a CMOS camera, or an sCMOS camera.

While not shown in FIG. 1, it should be understood that the apparatus 100 may optionally include any number of additional optical components including, but not limited to, one or more optical components selected from mirrors, lenses, windows, flats, diffusers, filters, collimators, polarizers, prisms, diffraction gratings, beamsplitters, and optical assemblies, any one or more of which may be optionally used in combination with the light source 110, the light-splitting device 120, the light trap 130, the interferometric optical assembly 140, or the recording device 150. For example, the apparatus 100 may include one or more polarization-management assemblies or systems for managing polarization of light before and/or after interaction with the surface of the article A, as well for optionally managing polarization of reference light. The one or more polarization-management assemblies or systems may include any number of polarization-management components including, but not limited to, one or more polarization-management components selected from polarization filters or polarizers (e.g., linear polarizers), polarization rotators or retarders (e.g., waveplates such as quarter-wave plates and half-wave plates), compensators (e.g., variable compensator), and photoelastic modulators. FIG. 9B provides a schematic illustrating an apparatus 900B optionally including one or more polarization-management systems or components thereof.

While not shown in FIG. 1, it should be understood that the apparatus 100 may include a processing means including, but not limited to, one or more computers or similar apparatus including primary and/or secondary memory and one or more processing elements operable to carry out arithmetic and logical operations. The one or more computers or similar apparatus may be individually selected from servers, workstations, desktop computers, nettops, laptops, netbooks, mobile devices including tablets and smartphones, and apparatus including graphics processing units ("GPU"s), application-specific integrated circuits ("ASIC"s), field-programmable gate arrays ("FPGA"s), or the like.

The processing means may include or have access to instructions for conveying articles to the apparatus 100; positioning articles for inspection, optionally including gradationally or continuously rotating articles for inspection; tuning optical components (e.g., piezoelectric-based components in polarization-management assemblies); switching the light source 110 on and off or otherwise between modes for providing light and not providing light; switching the recording device 150 on and off or otherwise between modes for detecting light and not detecting light; and/or synchronizing the light source 110 with the recording device 150.

The processing means may include or have access to instructions for processing electronic signals from the recording device 150 or an imaging device and/or image sensor thereof for detecting, distinguishing, and/or mapping features of articles. With respect to mapping features of articles, the processing means may generate a features map M corresponding to the electronic signals from the recording device 150 or an imaging device and/or image sensor thereof, an example of which is provided in FIG. 2. The features map M may provide, but is not limited to, three-dimensional surface imaging for constitutional features (e.g., air bearing surface of a slider) or defects (e.g., thermal asperities, pits, shallow surface defects, waviness, and the like in a hard disk surface), magnetic imaging, and measurements for the foregoing (e.g., thermal asperity height, waviness and the like in a hard disk surface). For example, the processing means may generate the features map M of FIG. 2, which corresponds to a surface of a hard disk with a lubricant layer defect.

The processing means may generate any of a number of features maps corresponding to the electronic signals from the recording device 150 or an imaging device and/or image sensor thereof, each of which features maps may provide differentiating or distinguishing information for one or more types of features about the surface of the article A. For example, the processing means may generate features maps $M_1$, $M_2$, $M_3$, ..., $M_n$, wherein n indicates the $n^{th}$ features map. The processing means may generate a composite features map from any two or more constituent features maps or the information sufficient to produce them. The composite features map may enhance one or more features common to the two or more constituent features maps. The composite features map may also consolidate one or more features onto the composite features map from any two or more constituent features maps including different features between them. The one-to-one-to-one correspondence provided herein among a particular, fixed area of a surface of an article A, a pixel of an image sensor, and a particular, fixed area of a features map M facilitates generating the one or more composite features maps.

The processing means may increase pixel resolution for one or more features maps with pixel interpolation. Pixel interpolation may increase pixel resolution about 10× or more over a native resolution for that of an imaging device and/or image sensor thereof without an increase in physical pixels.

The apparatus 100 of FIG. 1 may be configured to inspect articles for features at a rate commensurate with or greater than the rate at which the articles or workpieces thereof are produced. For example, the apparatus 100 may be configured to inspect articles at a rate of at least 1, 2, 3, 4, 5, 6, 7, 8, 9, 10, 12, 14, 16, 18, or 20 article(s) per second, or greater. Inspecting articles for features at a rate commensurate with or greater than the rate at which the articles or workpieces thereof are produced is a function of many features of the apparatus including, but not limited to, maintaining the linear and the angular position of articles while inspecting them.

In addition to the schematic of FIG. 1 illustrating the apparatus 100 and the number of components thereof, the schematic of FIG. 1 also illustrates methods for inspecting articles for features using interference in light reflected from the articles.

As shown in FIG. 1, the light source 110 may provide parallel light 112, of which outermost light rays a and b of FIG. 1 are representative. Focusing on light ray a with the understanding that light ray b follows an analogous path, light ray a may be conveyed to the light-splitting device 120, where a first portion of light ray a may be reflected to yield light ray $a_r$, and where a second portion of light ray a may be transmitted to yield light ray $a_t$. As further shown in FIG. 1, light ray $a_t$ may subsequently terminate in the light trap 130 while light ray $a_r$ may be conveyed through the interferometric optical assembly 140 to the surface of the article A where light ray $a_r$ or a derivative thereof may interact with and/or reflect from the surface of the article A. Depending upon the interferometric optical assembly 140, different embodiments for which are provided in reference to FIGS. 3A, 3B, 5, 8, 9A, and 9B, light ray $a_r$ may subsequently combine with a reference light ray in accordance with the superposition principle to yield light ray a. As further shown in FIG. 1, light ray $a_c$ may be subsequently conveyed back to and transmitted through the light-splitting device 120 to yield light ray $a_{ct}$. Light ray $a_{ct}$ may be subsequently conveyed to the recording device 150 where it may be converted to an electronic signal and processed by the processing means for generating a features map such as the features map M of FIG. 2.

In view of the apparatus 100 and the components thereof provided in reference to FIG. 1, some particular embodiments of the apparatus 100 will now be provided with some non-limiting, interferometric optical assemblies corresponding to the interferometric optical assembly 140.

FIGS. 3A and 3B provide schematics illustrating an apparatus 300 including a number of components for inspecting articles for features using interference in light reflected from the articles. Like the apparatus 100 shown in FIG. 1, the apparatus 300 shown in FIGS. 3A and 3B may include, but is not limited to, a light source 110, a light-splitting device 120, a light trap 130, an interferometric optical assembly 140, and a recording device 150. As further shown in FIGS. 3A and 3B, an article A may be positioned, for example, on a stage under the apparatus 300 where light from the light source 110 may illuminate, interact with, and reflect from a surface of the article A.

With respect to the interferometric optical assembly 140 of the apparatus 300, the interferometric optical assembly 140 may include, but is not limited to, a lens 342, a light-splitting device 344, and a mirror 346.

With respect to the lens 342, the lens 342 may include, but is not limited to, a telecentric lens, which reduces optical aberrations and feature-position errors for features in features maps such as the features map M of FIG. 2. The telecentric lens may include, but is not limited to, an object-space telecentric lens (i.e., entrance pupil at infinity), an image-space telecentric lens (i.e., exit pupil at infinity), or a bi-telecentric or double telecentric lens (i.e., entrance and exit pupils at infinity). For example, the lens 342 may be a bi-telecentric lens. It should be understood that the lens 342 is not limited to the foregoing, and any reference to the lens 342 used herein may include the lens 342 alone or the lens 342 in combination with one or more additional optical components provided herein in a lens assembly.

With respect to the light-splitting device 344, the light-splitting device 344 may include, but is not limited to, a light-splitting device such as the light-splitting device 120 provided in reference to FIG. 1. For example, the light-splitting device 344 may be a light-splitting cube as shown in FIGS. 3A and 3B. It should be understood that the light-splitting device 344 is not limited to the foregoing, and any reference to the light-splitting device 344 used herein may include the light-splitting device 344 alone or the light-splitting device 344 in combination with one or more additional optical components provided herein in a light-splitting assembly.

With respect to the mirror 346, the mirror 346 may include, but is not limited to, any optically coated flat or mirror operable to reflect incident light back toward the light-splitting device 344. For example, the mirror 346 may be a first-surface mirror, wherein a first surface of a mirror substrate facing the light-splitting device 344 may be optically coated with an optical coating to minimize energy loss to the mirror substrate, and wherein the optical coating may be optionally a broadband (e.g., 400-750 nm) coating with an average reflectance of at least 99% for one or more polarization states of light (e.g., p-polarized light and s-polarized light). The mirror 346 may be optionally mounted on an adjustable mount or stage such that the distance and/or angle of the mirror 346 to the light-splitting device 344 may be adjusted. It should be understood that the mirror 346 is not limited to the foregoing, and any reference to the mirror 346 used herein may include the mirror 346 alone or the mirror 346 in combination with one or more additional optical components provided herein in a mirror assembly.

In an alternative, the mirror 346 may include a digital micromirror device ("DMD") such as the DMD 446 of FIG. 4. The DMD 446 may include, but is not limited to, a mirror level 447 including a number of individually adjustable micrometer-sized (i.e., admits of μm units as measured in at least one dimension) mirrors or microscopic mirrors; a yoke-and-hinge level 448 including a number of yokes on torsion hinges onto which the microscopic mirrors may be respectively mounted; a yoke-address electrode level 449 including a number of yoke address electrodes in pairs respectively corresponding to the number of microscopic mirrors; and a substrate level including a number of CMOS-based, static random-access memory ("SRAM") cells respectively corresponding to the number of microscopic mirrors. The yoke-and-hinge level 448 may also include a number of mirror address electrodes in pairs respectively corresponding to the number of microscopic mirrors. A bias may be created among a pair of mirror address electrodes and a pair of yoke address electrodes to electrostatically lock a corresponding microscopic mirror in an initial position. The bias may be removed to tilt (e.g., ±10-12 or increments thereof) the microscopic mirror into a subsequent position in accordance with a charge in an underlying SRAM cell. The bias may be subsequently restored among the pair of mirror address electrodes and the pair of yoke address electrodes to electrostatically lock the microscopic mirror in the subsequent position.

In yet another alternative, the mirror 346 may include a spatial light modulator array ("SLMA") for selectably phase shifting light reflected therefrom.

Each microscopic mirror of the DMD 448 or element of the SLMA may have a one-to-one correspondence with a pixel of an image sensor of an imaging device. As provided herein, a pixel of an image sensor such as the foregoing pixel may also correspond to a particular, fixed area of a surface of an article A and a particular, fixed area of a features map M of the surface of the article A. In view of the foregoing, adjustment of a microscopic mirror of the DMD 446 or element of the SLMA may phase shift light (e.g., reference light) reflected therefrom, which, in turn, may result in a modification when the phase-shifted light combines with light reflected from the surface of the article A in a combination at the foregoing pixel of the image sensor. The modification in the combination may, in turn, result in a modification of the particular, fixed area of the features map M to which the foregoing pixel corresponds. As such, each individually adjustable microscopic mirror or any group of microscopic mirrors up to an including the entire DMD 446 provides a phase-shifting or phase-locking means for detailed inspection of a corresponding location on a surface of an article A through a corresponding features map M of the surface of the article A. Likewise, each individually adjustable element or any group of elements up to an including the entire SLMA provides a phase-shifting or phase-locking means for detailed inspection of a corresponding location on a surface of an article A through a corresponding features map M of the surface of the article A.

The DMD 446 may be optionally mounted on an adjustable mount or stage such that the distance and/or angle of the DMD 446 to the light-splitting device 344 may be adjusted. It should be understood that the DMD 446 is not limited to the foregoing, and any reference to the DMD 446 used herein may include the DMD 446 alone or the DMD 446 in combination with one or more additional optical components provided herein in a DMD assembly.

In addition to the schematics of FIGS. 3A and 3B illustrating the apparatus 300 and the number of components thereof, the schematics of FIGS. 3A and 3B also illustrate methods for inspecting articles for features using interference in light reflected from the articles.

As shown in FIG. 3A, the light source 110 may provide parallel light 112, of which outermost light rays a and b of FIG. 3A are representative. Focusing on light ray a, light ray a may be conveyed to the light-splitting device 120, where a first portion of light ray a may be reflected to yield light ray $a_r$, and where a second portion of light ray a may be transmitted to yield light ray $a_t$ provided in reference to FIG. 1. Light ray $a_r$ may be subsequently conveyed to the lens 342 where light ray $a_r$ may be illustratively refracted as shown in a direction away from the light source 110 and toward the light trap 130. It should be understood that the foregoing direction is for a non-limiting, illustrative purpose. Light ray $a_r$ may be subsequently conveyed to the light-splitting device 344, where a first portion of light ray $a_r$ may be reflected to yield light ray $a_{r,r}$ and where a second portion of light ray $a_r$ may be transmitted to yield light ray $a_{r,t}$. Light ray $a_{r,r}$, which corresponds to a reference light ray, may be subsequently conveyed to and reflected from the mirror 346 or DMD 446 to yield light ray $a_{r,r'}$. Meanwhile, light ray $a_{r,t}$ may be conveyed to the surface of the article A where the light ray $a_{r,t}$ may interact with and/or reflect from the surface of the article A to yield light ray $a_{r,t'}$. As further shown in FIG. 3A, each of light rays $a_{r,r'}$ and $a_{r,t'}$ may be subsequently conveyed back to the light-splitting device 344 where light rays $a_{r''}$ and $a_{r't}$ may combine in accordance with the superposition principle to yield light ray $a_c$. Light ray $a_c$ may be subsequently conveyed back to and transmitted through the light-splitting device 120 to yield light ray $a_{ct}$. Light ray $a_{ct}$ may be subsequently conveyed to the recording device 150 where it may be converted to an electronic signal and processed by the processing means for generating a features map such as the features map M of FIG. 2.

As shown in FIG. 3B, the light source 110 may provide parallel light 112, of which outermost light rays a and b of FIG. 3B are representative. Focusing on light ray b, light ray b may be conveyed to the light-splitting device 120, where a first portion of light ray b may be reflected to yield light ray $b_r$, and where a second portion of light ray b may be transmitted to yield light ray $b_t$ provided in reference to FIG. 1. Light ray $b_r$ may be subsequently conveyed to the lens 342 (e.g., bi-telecentric lens) where light ray $b_r$ may be illustratively refracted as shown in a direction toward the light source 110 and away from the light trap 130. It should be understood that the foregoing direction is for a non-limiting, illustrative purpose, and the foregoing direction is a different direction than that provided in reference to FIG. 3A. Light ray $b_r$ may be subsequently conveyed to the light-splitting device 344, where a first portion of light ray $b_r$ may be reflected to yield light ray $b_{r'}$, and where a second portion of light ray $b_r$ may be transmitted to yield light ray $b_{r't}$. Light ray $b_{r'}$, which corresponds to a reference light ray, may be subsequently conveyed to and reflected from the mirror 346 or DMD 446 to yield light ray $b_{r''}$. Meanwhile, light ray $b_{r't}$ may be conveyed to the surface of the article A where the light ray $b_{r't}$ may interact with and/or reflect from the surface of the article A to yield light ray $b_{r't}$. As further shown in FIG. 3B, each of light rays $b_{r''}$ and $b_{r't}$ may be subsequently conveyed back to the light-splitting device 344 where light rays $b_{r''}$ and $b_{r't}$ may combine in accordance with the superposition principle to yield light ray $b_c$. Light ray $b_c$ may be subsequently conveyed back to and transmitted through the light-splitting device 120 to yield light ray $b_{ct}$. Light ray $b_{ct}$ may be subsequently conveyed to the recording device 150 where it may be converted to an electronic signal and processed by the processing means for generating a features map such as the features map M of FIG. 2, which may be the same features map M provided in reference to FIG. 3A.

FIG. 5 provides a schematic illustrating an apparatus 500 including a number of components for inspecting articles for features using interference in light reflected from the articles. Like the apparatus 100 shown in FIG. 1, the apparatus 500 shown in FIG. 5 may include, but is not limited to, a light source 110, a light-splitting device 120, a light trap 130, an interferometric optical assembly 140, and a recording device 150. As further shown in FIG. 5, an article A may be positioned, for example, on a stage under the apparatus 500 where light from the light source 110 may illuminate, interact with, and reflect from a surface of the article A.

With respect to the interferometric optical assembly 140 of the apparatus 500, the interferometric optical assembly 140 may include, but is not limited to, a lens 342, a light-splitting device 544, and a mirror array 546.

With respect to the lens 342, the lens 342 may include, but is not limited to, a telecentric lens such as the telecentric lens provided in reference to FIGS. 3A and 3B. For example, the lens 342 may be a bi-telecentric lens. It should be understood that the lens 342 is not limited to the foregoing, and any reference to the lens 342 used herein may include the lens 342 alone or the lens 342 in combination with one or more additional optical components provided herein in a lens assembly.

With respect to the light-splitting device 544, the light-splitting device 544 may include, but is not limited to, a light-splitting device such as the light-splitting device 120 provided in reference to FIG. 1. For example, the light-splitting device 544 may be a light-splitting plate as shown in FIG. 5. It should be understood that the light-splitting device 544 is not limited to the foregoing, and any reference to the light-splitting device 544 used herein may include the light-splitting device 544 alone or the light-splitting device 544 in combination with one or more additional optical components provided herein in a light-splitting assembly.

With respect to the mirror array 546, the mirror array 546 may include, but is not limited to, a mirror array substrate including an array of reflective elements in the mirror array substrate and/or on the mirror array substrate, wherein the mirror array substrate is operable to transmit light therethrough, and wherein the array of reflective elements is operable to reflect incident light back toward the light-splitting device 544. The mirror array 546 may be optionally mounted on an adjustable mount or stage such that the distance and/or angle of the mirror array 546 to the light-splitting device 544 may be adjusted. It should be understood that the mirror array 546 is not limited to the foregoing, and any reference to the mirror array 546 used herein may include the mirror array 564 alone or the mirror array 546 in combination with one or more additional optical components provided herein in a lens assembly.

The mirror array 546 may include, but is not limited to, an array of micrometer-sized (i.e., admits of μm units as measured in at least one dimension) mirrors 547 on the mirror array substrate. The array of mirrors 547 may include first-surface mirrors at a first surface of the mirror array substrate facing the light-splitting device 544; second-surface mirrors at a second surface of the mirror array substrate behind the first surface with respect to the light-splitting device 544; or a combination of first-surface mirrors and second-surface mirrors. For example, the array of mirrors 547 may be an array of second-surface mirrors as shown in FIG. 5.

The array of mirrors 547 may include a patterned optical coating on the first-surface of the mirror array substrate and/or the second surface of the mirror array substrate, wherein the optical coating may be optionally a broadband (e.g., 400-750 nm) coating with an average reflectance of at least 99% for one or more polarization states of light (e.g., p-polarized light and s-polarized light). The patterned optical coating may provide any of a number of differently shaped mirrors in the array of mirrors 547 including, but not limited to, rectangle-shaped mirrors, square-shaped mirrors, or hexagon-shaped mirrors. For example, FIG. 6A provides a schematic illustrating a mirror array 646A including an array of mirrors 547 in which each mirror is a rectangle-shaped or square-shaped mirror 647A. For example, FIG. 6B provides a schematic illustrating a mirror array 646B including an array of mirrors 547 in which each mirror is a hexagon-shaped mirror 647B.

As provided herein, the mirror array 546 may be optionally mounted on an adjustable mount or stage such that the distance and/or angle of the mirror array 546 to the light-splitting device 544 may be adjusted. Additionally or alternatively, the mirror array 546 may be optionally mounted on a piezoelectric, XY-positioning stage such that the mirror array 546 may be translated in any XY-related direction over a distance corresponding to a sub-pixel-sized distance, a pixel-sized distance, or a multiple pixel-sized distance, wherein a pixel-sized distance corresponds to pixel size or pixel pitch in an image sensor of an imaging device. FIGS. 6A and 68 provide schematics illustrating translation of mirror arrays 646A and 646B, respectively. The processing means provided herein may be configured to generate a features map corresponding to each position into which the mirror array 546 is translated. The processing means may subsequently generate a composite features map from any two or more constituent features maps to enhance one or more features common to the two or more constituent features maps or consolidate one or more different features between the constituent features maps.

In an alternative, the mirror array 546 may include a liquid crystal-based mirror array such as the liquid crystal-based mirror array 746 of FIGS. 7A and 7B. The mirror array 746 may include, but is not limited to, an array of micrometer-sized (i.e., admits of μm units as measured in at least one dimension) liquid crystal cells 747. The array of cells 747 may include any of a number of differently shaped cells including, but not limited to, rectangle-shaped cells, square-shaped cells, or hexagon-shaped cells. For example, FIGS. 7A and 7B provide schematics illustrating the mirror array 746 including an array of cells 747 in which each cell is a hexagon-shaped cell as exemplified by cells 647A, 647B, and 647C.

The mirror array 746 may to be configured to electrically switch between any of a number of configurations in which the array of cells 747 includes cells of mixed reflective and transmissive states. For example, as shown in FIG. 7A, the mirror array 746 may be in a first configuration, wherein a first portion of the array of cells 747 may be in a reflective state as exemplified by the cell 747A, and wherein a second portion of the array of cells 747 may be in a transmissive state as exemplified by the cells 747B and 747C. As shown in FIG. 7B, the mirror array 746 may be electrically switched into a second configuration, wherein the first portion of the array of cells 747 may be in a transmissive state as exemplified by the cell 747A, wherein some of the second portion of the array of cells 747 may be in a reflective state as exemplified by the cell 747B, and wherein some of the second portion of the array of cells 747 may remain in the transmissive state as exemplified by the cell 747C. The processing means provided herein may be configured to generate a features map corresponding to each configuration into which the mirror array 746 is electrically switched. The processing means may subsequently generate a composite features map from any two or more constituent features maps to enhance one or more features common to the two or more constituent features maps or consolidate one or more different features between the constituent features maps.

In addition to the schematic of FIG. 5 illustrating the apparatus 500 and the number of components thereof, the schematic of FIG. 5 also illustrates methods for inspecting articles for features using interference in light reflected from the articles.

As shown in FIG. 5, the light source 110 may provide parallel light 112, of which outermost light rays a and b of FIG. 5 are representative. Focusing on light ray a, light ray a may be conveyed to the light-splitting device 120, where a first portion of light ray a may be reflected to yield light ray $a_r$, and where a second portion of light ray a may be transmitted to yield light ray $a_t$ provided in reference to FIG. 1. Light ray $a_r$ may be subsequently conveyed to the lens 342 where light ray $a_r$ may be illustratively refracted as shown in a direction away from the light source 110 and toward the light trap 130. It should be understood that the foregoing direction is for a non-limiting, illustrative purpose, and the foregoing direction may be a different direction such as that shown in FIG. 5 for light ray b. Light ray $a_r$ may be subsequently conveyed to and transmitted through the mirror array substrate of the mirror array 546 to the light-splitting device 544, where a first portion of light ray $a_r$ may be reflected to yield light ray $a_{r'}$, and where a second portion of light ray $a_r$ may be transmitted to yield light ray $a_{r't}$. Light ray $a_{r'}$, which corresponds to a reference light ray, may be subsequently conveyed to and reflected from a mirror 547 of the mirror array 546 to yield light ray $a_{r''}$. Meanwhile, light ray $a_{r't}$ may be conveyed to the surface of the article A where the light ray $a_{r't}$ may interact with and/or reflect from the surface of the article A to yield light ray $a_{r't'}$. As further shown in FIG. 5, each of light rays $a_{r''}$ and $a_{r't'}$ may be subsequently conveyed back to the light-splitting device 544 where light rays $a_{r''}$ and $a_{r't'}$ may combine in accordance with the superposition principle to yield light ray $a_c$. Light ray $a_c$ may be subsequently conveyed back to and transmitted through the light-splitting device 120 to yield light ray $a_{ct}$. Light ray $a_{ct}$ may be subsequently conveyed to the recording device 150 where it may be converted to an electronic signal and processed by the processing means for generating a features map such as the features map M of FIG. 2.

FIG. 8 provides a schematic illustrating an apparatus 800 including a number of components for inspecting articles for features using interference in light reflected from the articles. Like the apparatus 100 shown in FIG. 1, the apparatus 800 shown in FIG. 8 may include, but is not limited to, a light source 110, a light-splitting device 120, a light trap 130, an interferometric optical assembly 140, and a recording device 150. As further shown in FIG. 8, an article A may be positioned, for example, on a stage under the apparatus 800 where light from the light source 110 may illuminate, interact with, and reflect from a surface of the article A.

With respect to the interferometric optical assembly 140 of the apparatus 800, the interferometric optical assembly 140 may include, but is not limited to, a first lens 342, a polarizer 844, and a second lens 842.

With respect to the first lens 342, the first lens 342 may include, but is not limited to, a telecentric lens such as the telecentric lens provided in reference to FIGS. 3A and 3B. For example, the first lens 342 may be a bi-telecentric lens. It should be understood that the first lens 342 is not limited to the foregoing, and any reference to the first lens 342 used herein may include the first lens 342 alone or the first lens 342 in combination with one or more additional optical components provided herein in a lens assembly.

With respect to the polarizer 844, the polarizer 844 may include, but is not limited to, any light-splitting, light-polarizing device operable to split incident light into one or more different polarization states in one or more directions, respectively. The polarizer 844 may be optionally mounted on an adjustable mount or stage such that the distance and/or angle of the polarizer 844 to the first lens 342, the second lens 842, or both the first lens 342 and the second lens 842 may be adjusted. It should be understood that the polarizer 844 is not limited to the foregoing, and any reference to the polarizer 844 used herein may include the polarizer 844 alone or the polarizer 844 in combination with one or more additional optical components provided herein in a polarizer assembly.

The polarizer 844 may split incident light into a first portion with a first polarization state and a second portion with a second, different polarization state, and the polarizer 844 may simultaneously transmit the first portion in a first direction and the second portion in a second, optionally different direction. For example, the polarizer 844 may split the incident light into orthogonal, linearly polarized light including s-polarized light and p-polarized light, and the polarizer 844 may transmit the s-polarized light and the p-polarized light parallel to each other in the same direction, or the polarizer 844 may transmit the s-polarized light and the p-polarized light oblique (e.g., 15-45°) to each other in different directions. The composition, construction, or the composition and construction of the polarizer 844 determines the polarization states and directions into which the incident light is split, wherein the composition includes substrate, bonding, and/or coating compositions of the polarizer 844, and wherein the construction includes the manner in which one or more of the foregoing is assembled into the polarizer 844. The polarizer 844 may include, but is not limited to, a beam displacer (e.g., calcite-based prism optionally with one or more anti-reflective coatings), a Wollaston prism (e.g., two calcite-based prisms bonded together optionally with one or more anti-reflective coatings), or a number of beam displacers or Wollaston prisms in an array as provided in FIGS. 9A and 9B.

With respect to the second lens 842, the second lens 842 may be the same as or different than the first lens 342. The second lens 842 may include, but is not limited to, a telecentric lens such as the telecentric lens provided in reference to FIGS. 3A and 3B. For example, the second lens 842 may be a bi-telecentric lens. It should be understood that the second lens 842 is not limited to the foregoing, and any reference to the second lens 842 used herein may include the second lens 842 alone or the second lens 842 in combination with one or more additional optical components provided herein in a lens assembly.

In addition to the schematic of FIG. 8 illustrating the apparatus 800 and the number of components thereof, the schematic of FIG. 8 also illustrates methods for inspecting articles for features using interference in light reflected from the articles.

As shown in FIG. 8, the light source 110 may provide parallel light 112, of which inner light ray a of FIG. 8 is representative. Light ray a may be conveyed to the light-splitting device 120, where a first portion of light ray a may be reflected to yield light ray $a_r$, and where a second portion of light ray a may be transmitted to yield light ray $a_t$ provided in reference to FIG. 1. Light ray $a_r$ may be subsequently conveyed to the lens 342 where light ray $a_r$ may be illustratively refracted as shown in a direction away from the light source 110 and toward the light trap 130. It should be understood that the foregoing direction is for a non-limiting, illustrative purpose, and the foregoing direction may be a different direction such as that provided herein. Light ray $a_r$ may be subsequently conveyed to the polarizer 844, where a first portion of light ray $a_r$ may be split to yield light ray $a_p$, and where a second portion of light ray $a_r$ may be split to yield light ray $a_{p'}$, which corresponds to a reference light ray orthogonal to light ray $a_p$. Light rays $a_p$ and $a_{p'}$ may be subsequently refracted through the lens 842 and conveyed to the surface of the article A where the light rays $a_p$ and $a_{p'}$ may interact with and/or reflect from adjacent locations on the surface of the article A to yield light rays $a_{pr}$ and $a_{p'r}$. As further shown in FIG. 8, light rays $a_{pr}$ and $a_{p'r}$ may be subsequently refracted through the lens 842 and conveyed to the polarizer 844 where the light rays $a_{pr}$ and $a_{p'r}$ may combine in accordance with the superposition principle to yield light ray $a_c$. Light ray $a_c$ may be subsequently conveyed back to and transmitted through the light-splitting device 120 to yield light ray $a_{ct}$. Light ray $a_{ct}$ may be subsequently conveyed to the recording device 150 where it may be converted to an electronic signal and processed by the processing means for generating a features map such as the features map M of FIG. 2.

FIGS. 9A and 9B provide schematics respectively illustrating an apparatus 900A and an apparatus 900B, each of which includes a number of components for inspecting articles for features using interference in light reflected from the articles. Like the apparatus 100 shown in FIG. 1, each of the apparatus 900A and the apparatus 900B may individually include, but is not limited to, a light source 110, a light-splitting device 120, a light trap 130, an interferometric optical assembly 140, and a recording device 150. As further shown in FIGS. 9A and 9B, an article A may be positioned, for example, on a stage under the apparatus 900A or the apparatus 900B where light from the light source 110 may illuminate, interact with, and reflect from a surface of the article A.

With respect to the interferometric optical assembly 140, each of the apparatus 900A and the apparatus 900B individually includes a non-limiting combination of components for the interferometric optical assembly 140 provided in reference to at least FIGS. 3A, 3B, and 8. As shown in FIGS. 9A and 9B, the interferometric optical assembly 140 may include, but is not defined by or limited to, a lens 342, a light-splitting device 344, a polarizer 844, a second lens 842, and a mirror 346.

With respect to the first lens 342, the first lens 342 may include, but is not limited to, a telecentric lens such as the telecentric lens provided in reference to FIGS. 3A and 3B. For example, the first lens 342 may be a bi-telecentric lens. It should be understood that the first lens 342 is not limited to the foregoing, and any reference to the first lens 342 used herein may include the first lens 342 alone or the first lens 342 in combination with one or more additional optical components provided herein in a lens assembly.

With respect to the light-splitting device 344, the light-splitting device 344 may include, but is not limited to, a light-splitting device such as the light-splitting device 120 provided in reference to FIG. 1. For example, the light-splitting device 344 may be a light-splitting cube as shown in FIGS. 9A and 9B. It should be understood that the light-splitting device 344 is not limited to the foregoing, and any reference to the light-splitting device 344 used herein may include the light-splitting device 344 alone or the light-splitting device 344 in combination with one or more additional optical components provided herein in a light-splitting assembly.

With respect to the polarizer 844, the polarizer 844 may include, but is not limited to, the polarizer 844 provided in reference to FIG. 8. For example, the polarizer 844 may be a beam displacer, a Wollaston prism, or a number of beam displacers or Wollaston prisms in an array as provided in FIGS. 9A and 9B. It should be understood that the polarizer 844 is not limited to the foregoing, and any reference to the polarizer 844 used herein may include the polarizer 844 alone or the polarizer 844 in combination with one or more additional optical components provided herein in a polarizer assembly.

With respect to the second lens 842, the second lens 842 may be the same as or different than the first lens 342. The second lens 842 may include, but is not limited to, a telecentric lens such as the telecentric lens provided in reference to FIGS. 3A and 3B. For example, the second lens 842 may be a bi-telecentric lens. It should be understood that the second lens 842 is not limited to the foregoing, and any reference to the second lens 842 used herein may include the second lens 842 alone or the second lens 842 in combination with one or more additional optical components provided herein in a lens assembly.

With respect to the mirror 346, the mirror 346 may include, but is not limited to, the mirror 346 provided in reference to FIGS. 3A and 3B. For example, the mirror 346 may be a first-surface mirror or a DMD. It should be understood that the mirror 346 is not limited to the foregoing, and any reference to the mirror 346 used herein may include the mirror 346 alone or the mirror 346 in combination with one or more additional optical components provided herein in a mirror assembly.

As provided in reference to the apparatus 100 of FIG. 1, apparatus provided herein may include one or more polarization-management assemblies or systems for managing polarization of light before and/or after interaction with the surface of the article A, as well for optionally managing polarization of reference light. The one or more polarization-management assemblies or systems may include any number of polarization-management components including, but not limited to, one or more polarization-management components selected from polarization filters or polarizers (e.g., linear polarizers), polarization rotators or retarders (e.g., waveplates such as quarter-wave plates and half-wave plates), compensators (e.g., variable compensator), and photoelastic modulators. It should be understood that the polarization-management assemblies or systems are not limited to the foregoing, and any reference to the polarization-management assemblies or systems used herein may include one or more additional optical components provided herein in the polarization-management assemblies or systems.

FIG. 9B provides a schematic illustrating an apparatus 900B optionally including one or more polarization-management systems or components thereof. As shown in FIG. 9B, the apparatus 900B may optionally include a first polarization-management system for managing polarization of light before interaction with the surface of the article A, wherein the first polarization-management system includes a polarization rotator 952. As further shown in FIG. 9B, the apparatus 900B may optionally include a second polarization-management system for managing polarization of reference light, wherein the second polarization-management system includes a polarization rotator 954 and/or polarization filter 956. As further shown in FIG. 9B, the apparatus 900B may optionally include a third polarization-management system for managing polarization of light after interaction with the surface of the article A, wherein the third polarization-management system includes a polarization filter 958. It should be understood that the foregoing polarization-management systems and/or the components thereof are not limited to the apparatus 900B, and any apparatus provided herein may include one or more of the polarization-management systems and/or the components thereof.

While the schematics of FIGS. 9A and 9B respectively illustrate the apparatus 900A and 900B and the number of components thereof, the schematics do not expressly illustrate methods for inspecting articles for features using interference in light reflected from the articles. However, the methods for inspecting articles for features using interference in light reflected from the articles may be provided with reference to FIGS. 3A, 3B, and 8.

As shown in FIG. 9, the light source 110 may provide parallel light 112, of which light ray a of FIGS. 3A, 3B, and 8 is representative. Focusing on light ray a of FIGS. 3A and 3B, light ray a may be conveyed to the light-splitting device 120, optionally through the polarization rotator 952 first, where a first portion of light ray a may be reflected to yield light ray $a_r$, and where a second portion of light ray a may be transmitted to yield light ray $a_t$ provided in reference to FIG. 1. Light ray $a_r$ may be subsequently conveyed to the lens 342 where light ray $a_r$ may be illustratively refracted as shown in a direction away from the light source 110 and toward the light trap 130. It should be understood that the foregoing direction is for a non-limiting, illustrative purpose. Light ray $a_r$ may be subsequently conveyed to the light-splitting device 344, where a first portion of light ray $a_r$ may be reflected to yield light ray $a_{r'}$, and where a second portion of light ray $a_r$ may be transmitted to yield light ray $a_{rt}$. Light ray $a_{r'}$ may be subsequently conveyed to the mirror 346 or DMD 446, optionally through the polarization rotator 954 and the polarization filter 956 first, and reflected from the mirror 346 or DMD 446 to yield light ray $a_{r''}$. Meanwhile, light ray $a_{rt}$ may be conveyed to the polarizer 844 shown in FIGS. 9A and 9B, where a first portion of light ray $a_{rt}$ may be split to yield light ray $a_p$ shown in FIG. 8, and where a second portion of light ray $a_{rt}$ may be split to yield orthogonal light ray $a_{p'}$ shown in FIG. 8. Focusing on light rays $a_p$ and $a_{p'}$ of FIG. 8, light rays $a_p$ and $a_{p'}$ may be subsequently refracted through the lens 842 and conveyed to the surface of the article A where the light rays $a_p$ and $a_{p'}$ may interact with and/or reflect from adjacent locations on the surface of the article A to yield light rays $a_{pr}$ and $a_{p'r}$. Light rays $a_{pr}$ and $a_{p'r}$ may be subsequently refracted through the lens 842 and conveyed to the polarizer 844 where the light rays $a_{pr}$ and $a_{p'r}$ may combine in accordance with the superposition principle to yield light ray $a_c$. Each of light rays $a_c$ (FIG. 8) and $a_{r''}$ (FIGS. 3A and 3B) may be subsequently conveyed back to the light-splitting device 344 where light rays $a_c$ and $a_{r''}$ may combine in accordance with the superposition principle. The combination of light ray $a_c$ and light ray $a_{r''}$ may be subsequently conveyed back to and transmitted through the light-splitting device 120 to yield light ray $a_{ct}$. Light ray $a_{ct}$ may be subsequently conveyed to the recording device 150, optionally through the polarization filter 958 first, where it may be converted to an electronic signal and processed by the processing means for generating a features map such as the features map M of FIG. 2.

As such, provided herein is a method comprising conveying parallel light along a primary axis through a telecentric lens and a light-splitting device, respectively; illuminating a majority of a surface of an article with the parallel light; conveying reflected light from the surface of the article along the primary axis back through the light-splitting device and the telecentric lens, respectively; and recording interference resulting from a combination of light comprising at least the reflected light from the surface of the article. In some embodiments, the telecentric lens is a bi-telecentric lens. In some embodiments, the light-splitting device produces orthogonal, linearly polarized light from the parallel light. In some embodiments, the method further comprises conveying the polarized light along the primary axis through another telecentric lens before illuminating the majority of the surface of the article. In some embodiments, height differences in one or more surface features of the surface of the article provide different path lengths for the polarized light and produce phase differences in the reflected light from the surface of the article. In some embodiments, recording interference resulting from the combination of light comprises imaging the interference from the phase differences in the reflected light from the surface of the article. In some embodiments, the light-splitting device transmits a first portion of the parallel light and reflects a second portion the parallel light. In some embodiments, the method further comprises reflecting the second portion of the parallel light from one or more mirrors placed along the primary axis or one or more mirrors placed along a secondary axis at an angle to the primary axis. In some embodiments, the combination of light comprising at least the reflected light from the surface of the article further comprises the second portion of the parallel light after reflecting the second portion of the parallel light from the one or more mirrors. In some embodiments, recording interference resulting from the combination of light comprises imaging the interference from phase differences in the combination of the reflected light from the surface of the article and the second portion of the parallel light after reflecting the second portion of the parallel light from the one or more mirrors.

Also provided herein is a method, comprising conveying parallel light through a telecentric lens and a light-splitting device, respectively, wherein the light-splitting device transmits a surface-interactive portion of the parallel light and reflects a reference portion of the parallel light toward a mirror array; illuminating a majority of a surface of an article with the surface-interactive portion of the parallel light; conveying reflected light from the surface of the article back through the light-splitting device and the telecentric lens, respectively; and recording interference resulting from a combination of the reflected light from the surface of the article and the reference portion of the parallel light subsequent to reflection from the mirror array. In some embodiments, the telecentric lens is a bi-telecentric lens, and the light-splitting device is a beam splitter plate. In some embodiments, the mirror array comprises an array of rectangle-shaped mirrors mounted on a piezoelectric, XY-positioning stage. In some embodiments, the mirror array comprises an array of hexagonal-shaped mirrors mounted on a piezoelectric, XY-positioning stage. In some embodiments, the mirror array comprises an array of liquid crystal cells configured to electrically switch between reflective and transmissive states.

Also provided herein is a method, comprising conveying parallel light along a primary axis through a telecentric lens and a light-splitting device, respectively, wherein the light-splitting device transmits a surface-interactive portion of the parallel light and reflects a reference portion of the parallel light toward a tilted mirror; illuminating a majority of a surface of an article with the surface-interactive portion of the parallel light; conveying reflected light from the surface of the article back through the light-splitting device and the telecentric lens, respectively; and recording interference resulting from a combination of the reflected light from the surface of the article and the reference portion of the parallel light subsequent to reflection from the tilted mirror. In some embodiments, the telecentric lens is a bi-telecentric lens. In some embodiments, the light-splitting device is a beam splitter cube. In some embodiments, the tilted mirror comprises an array of individually adjustable, rectangle-shaped mirrors. In some embodiments, each of the rectangle-shaped mirrors may be locked in position for phase locking with respect to a corresponding location on the surface of the article.

While some particular embodiments have been provided herein, and while these particular embodiments have been provided in considerable detail, it is not the intention for these particular embodiments to limit the scope of the concepts provided herein. Additional adaptations and/or modifications may appear to persons having ordinary skill in the art, and, in broader aspects, these adaptations and/or modifications may be encompassed as well. Accordingly, departures may be made from the foregoing embodiments without departing from the scope of the concepts provided herein.

What is claimed is:

1. A method, comprising:
conveying parallel light along a primary axis through a telecentric lens and a light-splitting device, respectively;
illuminating a majority of a surface of an article with the parallel light, wherein the majority of the surface is greater than 50% of the surface;
conveying reflected light from the surface of the article along the primary axis back through the light-splitting device and the telecentric lens, respectively;
recording interference resulting from a combination of light comprising at least the reflected light from the surface of the article; and
generating a features map corresponding to the recording, wherein the features map includes three-dimensional surface images of a hard drive air bearing surface.

2. The method of claim 1,
wherein the telecentric lens is a bi-telecentric lens.

3. The method of claim 2,
wherein the light-splitting device produces orthogonal, linearly polarized light from the parallel light.

4. The method of claim 3, further comprising
conveying the polarized light along the primary axis through another telecentric lens before illuminating the majority of the surface of the article.

5. The method of claim 3,
wherein height differences in one or more surface features of the surface of the article provide different path lengths for the polarized light and produce phase differences in the reflected light from the surface of the article.

6. The method of claim 5,
wherein recording interference resulting from the combination of light comprises imaging the interference from the phase differences in the reflected light from the surface of the article.

7. The method of claim 2,
wherein the light-splitting device transmits a first portion of the parallel light and reflects a second portion the parallel light.

8. The method of claim 7, further comprising
reflecting the second portion of the parallel light from one or more mirrors placed along the primary axis or one or more mirrors placed along a secondary axis at an angle to the primary axis.

9. The method of claim 8,
wherein the combination of light comprising at least the reflected light from the surface of the article further comprises the second portion of the parallel light after reflecting the second portion of the parallel light from the one or more mirrors.

10. The method of claim 9,
wherein recording interference resulting from the combination of light comprises imaging the interference from phase differences in the combination of the reflected light from the surface of the article and the second portion of the parallel light after reflecting the second portion of the parallel light from the one or more mirrors.

11. A method, comprising:
conveying parallel light through a telecentric lens and a light-splitting device, respectively, wherein the light-splitting device transmits a surface-interactive portion of the parallel light and reflects a reference portion of the parallel light toward a mirror array;
illuminating a majority of a surface of an article with the surface-interactive portion of the parallel light, wherein the majority of the surface is greater than 50% of the surface;
conveying reflected light from the surface of the article back through the light-splitting device and the telecentric lens, respectively;
recording interference resulting from a combination of the reflected light from the surface of the article and the reference portion of the parallel light subsequent to reflection from the mirror array; and
generating a features map corresponding to the recording, wherein the features map includes surface images of a magnetic recording read-write head or a hard disk surface.

12. The method of claim 11,
wherein the telecentric lens is a bi-telecentric lens, and
wherein the light-splitting device is a beam splitter plate.

13. The method of claim 11,
wherein the mirror array comprises an array of rectangle-shaped mirrors mounted on a piezoelectric, XY-positioning stage.

14. The method of claim 11,
wherein the mirror array comprises an array of hexagonal-shaped mirrors mounted on a piezoelectric, XY-positioning stage.

15. The method of claim 11,
wherein the mirror array comprises an array of liquid crystal cells configured to electrically switch between reflective and transmissive states.

16. A method, comprising:
conveying parallel light along a primary axis through a telecentric lens and a light-splitting device, respectively,
wherein the light-splitting device transmits a surface-interactive portion of the parallel light and reflects a reference portion of the parallel light toward a tilted mirror;
illuminating a majority of a surface of an article with the surface-interactive portion of the parallel light, wherein the majority of the surface is greater than 50% of the surface;
conveying reflected light from the surface of the article back through the light-splitting device and the telecentric lens, respectively;
recording interference resulting from a combination of the reflected light from the surface of the article and the reference portion of the parallel light subsequent to reflection from the tilted mirror; and
generating a features map corresponding to the recording, wherein the features map includes an image of a hard drive surface, subsurface, or magnetic defect.

17. The method of claim 16,
wherein the telecentric lens is a bi-telecentric lens.

18. The method of claim 16,
wherein the light-splitting device is a beam splitter cube.

19. The method of claim 16,
wherein the tilted mirror comprises an array of individually adjustable, rectangle-shaped mirrors.

20. The method of claim 16,
wherein each of the rectangle-shaped mirrors may be locked in position for phase locking with respect to a corresponding location on the surface of the article.

* * * * *